(12) United States Patent
Vandermeulen

(10) Patent No.: US 12,318,499 B2
(45) Date of Patent: Jun. 3, 2025

(54) METHODS AND SYSTEMS FOR MEDICAL PLASMA TREATMENT AND GENERATION OF PLASMA ACTIVATED MEDIA

(71) Applicant: Peter F. Vandermeulen, Newburyport, MA (US)

(72) Inventor: Peter F. Vandermeulen, Newburyport, MA (US)

(*) Notice: Subject to any disclaimer, the term of this patent is extended or adjusted under 35 U.S.C. 154(b) by 1100 days.

(21) Appl. No.: 17/193,648

(22) Filed: Mar. 5, 2021

(65) Prior Publication Data

US 2021/0283290 A1    Sep. 16, 2021

Related U.S. Application Data

(60) Provisional application No. 62/989,053, filed on Mar. 13, 2020.

(51) Int. Cl.
*H01J 37/32* (2006.01)
*A61L 2/00* (2006.01)
(Continued)

(52) U.S. Cl.
CPC ............... *A61L 2/14* (2013.01); *A61L 2/0094* (2013.01); *A61N 1/44* (2013.01);
(Continued)

(58) Field of Classification Search
CPC ...... A61L 2/14; A61L 2/0094; A61L 2202/11; A61L 2202/14; A61L 2202/15; A61L 2202/21; A61L 2/0011; A61L 2202/22; A61L 2202/24; A61N 1/44; H01J 37/32192; H01J 37/02; H05H 2245/34;
(Continued)

(56) References Cited

U.S. PATENT DOCUMENTS 3,999,097 A   12/1976   Ko et al.
4,185,213 A    1/1980   Scannell
(Continued)

FOREIGN PATENT DOCUMENTS

CN       101553897 A      10/2009
KR    2005-0117576 A      12/2005
(Continued)

OTHER PUBLICATIONS

"Photovoltaic Systems," ISBN 978-0-8269-1287-9, 2007.
(Continued)

*Primary Examiner* — Rudy Zervigon
(74) *Attorney, Agent, or Firm* — Alexander Akhiezer; Foley Hoag LLP

(57) ABSTRACT

A membrane plate assembly is disclosed for use with a cold atmospheric plasma applicator to expose a medium to plasma beams from the plasma applicator. The membrane plate assembly includes a membrane plate stack configured to receive the plasma beams from the plasma applicator. The membrane plate stack includes a plurality of membrane-covered structures facing each other in a generally parallel arrangement and being spaced apart to define a channel therebetween through which the plasma beams are directed. Each membrane-covered structure includes a structure and a membrane covering outer surfaces of the structure with a gap therebetween through which the medium is flowed.

12 Claims, 13 Drawing Sheets

(51) Int. Cl.
*A61L 2/14* (2006.01)
*A61N 1/44* (2006.01)
*H01J 37/02* (2006.01)

(52) U.S. Cl.
CPC ..... *H01J 37/32192* (2013.01); *A61L 2202/11* (2013.01); *A61L 2202/14* (2013.01); *A61L 2202/15* (2013.01); *A61L 2202/21* (2013.01); *H01J 37/02* (2013.01)

(58) Field of Classification Search
CPC .... H05H 2245/36; H05H 1/30; H05H 1/4622; H05H 1/463; C23C 16/511
USPC .................. 118/723 MW, 723 ME, 723 MR, 118/723 MA; 156/345.36, 345.41
See application file for complete search history.

(56) References Cited

U.S. PATENT DOCUMENTS

| | | | |
|---|---|---|---|
| 4,268,801 | A | 5/1981 | Stappaerts |
| 4,450,031 | A | 5/1984 | Ono et al. |
| 4,512,868 | A | 4/1985 | Fujimura et al. |
| 4,883,686 | A * | 11/1989 | Doehler ............ C23C 16/45514 427/523 |
| 5,126,575 | A | 6/1992 | White |
| 5,311,103 | A | 5/1994 | Asmussen et al. |
| 5,389,153 | A | 2/1995 | Paranjpe et al. |
| 5,538,699 | A | 7/1996 | Suzuki |
| 5,702,530 | A | 12/1997 | Shan et al. |
| 5,783,102 | A | 7/1998 | Keller |
| 5,843,236 | A | 12/1998 | Yoshiki et al. |
| 5,868,849 | A | 2/1999 | Nakao |
| 5,945,677 | A | 8/1999 | Leung et al. |
| 6,028,393 | A * | 2/2000 | Izu ....................... C23C 16/517 315/111.21 |
| 6,114,811 | A | 9/2000 | Wu |
| 6,204,606 | B1 | 3/2001 | Spence et al. |
| 6,298,806 | B1 | 10/2001 | Moisan et al. |
| 6,444,105 | B1 | 9/2002 | Lai et al. |
| 6,497,783 | B1 | 12/2002 | Suzuki et al. |
| 6,558,504 | B1 | 5/2003 | Markunas et al. |
| 6,796,268 | B2 | 9/2004 | Ishii |
| 7,305,935 | B1 | 12/2007 | Foster |
| 7,311,796 | B2 | 12/2007 | Goto et al. |
| 7,723,637 | B2 | 5/2010 | Ohmi et al. |
| 8,800,483 | B2 | 8/2014 | Vandermeulen |
| 10,490,386 | B2 | 11/2019 | Vandermeulen |
| 10,727,031 | B2 | 7/2020 | Vandermeulen |
| 10,861,667 | B2 | 12/2020 | Vandermeulen |
| 10,861,669 | B2 | 12/2020 | Vandermeulen |
| 2002/0020691 | A1* | 2/2002 | Jewett ............... H01J 37/32009 219/121.43 |
| 2003/0066487 | A1 | 4/2003 | Suzuki |
| 2003/0234369 | A1 | 12/2003 | Glukhoy |
| 2004/0071613 | A1 | 4/2004 | Goto et al. |
| 2005/0257891 | A1 | 11/2005 | Goto et al. |
| 2005/0258380 | A1 | 11/2005 | White et al. |
| 2006/0113494 | A1 | 6/2006 | Chen et al. |
| 2007/0054064 | A1 | 3/2007 | Ohmi et al. |
| 2007/0193517 | A1 | 8/2007 | Matsuuchi et al. |
| 2008/0017616 | A1 | 1/2008 | Lee et al. |
| 2008/0078954 | A1 | 4/2008 | Vanderberg et al. |
| 2008/0149826 | A1 | 6/2008 | Renau et al. |
| 2008/0220558 | A1 | 9/2008 | Zehavi et al. |
| 2009/0029503 | A1 | 1/2009 | Arai et al. |
| 2009/0108198 | A1 | 4/2009 | Satoh et al. |
| 2010/0243879 | A1 | 9/2010 | Huang et al. |
| 2011/0005461 | A1* | 1/2011 | Vandermeulen ........ H01J 37/08 315/111.21 |
| 2012/0235569 | A1* | 9/2012 | Lee .......................... H05H 1/46 219/121.48 |
| 2012/0243879 | A1 | 9/2012 | Nashimoto et al. |
| 2013/0001414 | A1 | 1/2013 | Benveniste et al. |
| 2013/0002137 | A1 | 1/2013 | Tanibata et al. |
| 2013/0032574 | A1 | 2/2013 | Liu et al. |
| 2013/0043121 | A1 | 2/2013 | Anders |
| 2015/0087140 | A1 | 3/2015 | Nozawa et al. |
| 2018/0076009 | A1 | 3/2018 | Vandermeulen |
| 2018/0374670 | A1* | 12/2018 | Vandermeulen ........ H01J 37/05 |
| 2020/0058463 | A1 | 2/2020 | Vandermeulen |
| 2020/0090898 | A1* | 3/2020 | Vandermeulen .... H01J 37/3171 |
| 2020/0197566 | A1 | 6/2020 | Allain et al. |
| 2021/0283290 | A1 | 9/2021 | Vandermeulen |

FOREIGN PATENT DOCUMENTS

| | | |
|---|---|---|
| KR | 2008-0030100 A | 4/2008 |
| KR | 10 2013/0023588 A | 3/2013 |
| WO | WO-2007146395 A2 | 12/2007 |
| WO | WO-2008/018159 A1 | 2/2008 |
| WO | WO-2019/005288 A1 | 1/2019 |
| WO | WO-2021/183373 A1 | 9/2021 |

OTHER PUBLICATIONS

"Photovoltaics Design and Installation Manual," ISBN: 978-0-86571-520-2, 2004.

Bauer et al., "Cold Atmospheric Plasma and Plasma-Activated Medium Trigger RONS-Based Tumor Cell Apoptosis," Sci. Rep., 9(Article No. 14210): 1-28 (2019).

Bourdens et al., "Short exposure to cold atmospheric plasma induces senescence in human skin fibroblasts and adipose mesenchymal stromal cells," Sci. Rep., 9(8671): 1-15 (2019).

Geller, "Electron Cyclotron Resonance Ion Sources and ECR Plasmas," ISBN 0-7503-0107-4, 1996.

Heimann, "Plasma Spray Coating," ISBN: 978-3-527-32050-9, 2008.

International Search Report and Written Opinion for International Application No. PCT/US2018/030632 dated Aug. 24, 2018.

International Search Report and Written Opinion for PCT/US2010/034094 dated Jan. 3, 2011.

Izadjoo et al., "Medical applications of cold atmospheric plasma: State of the science," J. Wound Care, 27(Sup9): S4-S10 (2018).

Kaim, et al., "The Extrion 220 Parallel Scan Magnet," Report No. 195 Semiconductor Equipment, Presented at the 8th International Conference on Ion Implant Technology, July 30-Aug. 3, 1980, Surrey, U.K., pp. 1-5.

Kakoschke, et al., "Trench Sidewall Implantation with a Parallel Scanned Ion Beam," Report No. 195 Semiconductor Equipment Group, Published in IEEE trans. Elec. Dev., Nov. 1989, pp. 1-6.

Klämpfl et al., "Cold atmospheric air plasma sterilization against spores and other microorganisms of clinical interest," Appl. Environ. Microbiol., 78(15): 5077-5082 (2012).

Maisch et al., "Decolonisation of MRSA, *S. aureus* and *E. coli* by cold-atmospheric plasma using a porcine skin model in vitro," PLoS One, 7(4): e34610 (2012).

Markvart, et al., "Solar Cells, Materials, Manufacture and Operation," ISBN 1856174573, 2005.

Nakase, Kiyotaka et al. "Sheet-shaped ECR plasma generation using permanent 1-37 magnets for material processing," Thin Solid Films, Aug. 1, 1996, vol. 281-282, pp. 152-154.

Office Action for U.S. Appl. No. 14/341,450, issued Sep. 19, 2016.

Popov, "High Density Plasma Sources, Design, Physics and Performance," ISBN 0-8155-1377-1, 1995.

Vandermeulen, "A System and Applications Overview of Extrion 220 Medium Current Ion Implanter," Apr. 1990, 9 pgs.

Vandermeulen, "Een Campargue-Expansi Van Een Seeded Beam Van 90% Helium En 10% Stikstoff," Stageverslag Vdf/No. 85-12 (Dec. 1985), 80 pgs.

Vandermeulen, "Energy Contamination Control in a Medium Current Ion Implanter: First Results of an Experiment to match Electrical and SIMS Measurements on an E500 Medium Current Ion Implanter," Report No. 211 Semiconductor Equipment, Published in Semiconductor World Magazine, Nov. 1991, pp. 1-4.

Vandermeulen, "Energy Contamination Control in Multiple Charged Ion Implantations," Jun. 1992, 4 pgs.

(56) References Cited

OTHER PUBLICATIONS

Vandermeulen, et al., "Energy contamination of P2+ ion beams on the Varian, Extrion 220 medium current implanter," Nuclear Instruments and Methods in Physics Research B55 (1991) pp. 45-48 North Holland.
Wenham, et al., "Applied Photovoltaics," ISBN-10: 1-84407-401-3, 2007.
Xiong, "Cold Atmospheric Pressure Plasmas (CAPs) for Skin Wound Healing," Plasma Med.—Concepts Clin. Appl., pp. 121-140 (2018).
International Search Report and Written Opinion for International Application No. PCT/US2021/020998 mailed Jun. 28, 2021.
Stoffels et al., "Delayed Effects of Cold Atmospheric Plasma on Vascular Cells," Plasma Processes and Plymers, 5(6): 599-605 (2008).

* cited by examiner

METHODS AND SYSTEMS FOR MEDICAL PLASMA TREATMENT AND GENERATION OF PLASMA ACTIVATED MEDIA

CROSS REFERENCE TO RELATED APPLICATION

This application claims priority from U.S. Provisional Patent Application No. 62/989,053 filed on Mar. 13, 2020 entitled METHODS AND SYSTEMS FOR MEDICAL PLASMA TREATMENT AND GENERATION OF PLASMA ACTIVATED MEDIUM, which is hereby incorporated by reference.

BACKGROUND

The present application generally relates to methods and systems for deposition of plasma species on surfaces, and the treatment of objects and surfaces using plasmas in vacuum or atmospheric plasma treatment of medical surfaces such as skin cancers, wounds, and sterilization of those surfaces as well as to the use of plasma sources to create plasma activated media, which in turn can be injected into tissues such as solid cancers or blood.

Cold Atmospheric Plasma (CAP) sources are starting to get used for the treatment of virus- and antibiotic-resistant-bacterial infections, skin infections, large area wounds such as ulcers, burns, melanomas, and other wounds and cancers that can lead to infections and possibly sepsis. CAPs have been demonstrated to have a very promising effect on human dermal fibroblasts, accelerate wound healing and can lead to decolonization of (antibiotic resistant) MRSA, VRE, CRE and *E. coli* on skin and have been shown to result in the selective killing of melanoma and many other cancer cells either through direct plasma treatment or through the treatment of cancers by Plasma Activated Media (PAM) [1], [2]. Current state of the art plasma sources are primarily based on Dielectric Barrier Discharge (DBD) devices [1] which are small, sharp, pencil shaped cold atmospheric plasma sources. Although proven to be effective on small areas, such devices are difficult to use on large areas such as wounds or ulcerous infections. One cannot easily observe the effects of the treatment and it is therefore easy to miss an area. DBD plasmas often use gas mixtures of Argon, Helium, Nitrogen and Oxygen to generate a host of reactive gas species such as Ions ($O^+$, $N^+$, $O^-$, $N^-$, $NO_2^-$, etc.), Neutrals: ($O_2$, $N_2$, NO, Ozone), Radicals (O, N, OH, and metastable $He^*$, $Ar^*$). RONS (Reactive Oxygen and Nitrogen Species) such as O, $O^*$, N, $N^*$, $NO^*$, etc. have an electron in a non-ground state orbital or are reactive because of their need to bind an electron and can easily be ionized but can also decay back to the ground state.

In CAP treatment of biological cells, it is believed that higher energy radicals such as $He^*$ and RONS have the ability to diffuse over relatively large distances in atmosphere, whereas ions are neutralized fairly easily but likely fall back to a radical state first, rather than straight to a ground state. A relatively high energy $He^*$ or $Ar^*$ radical can decay to the ground state by interacting with an $O^*$ thereby possibly re-ionizing the $O^*$ into $O^+$ and a free electron. It is well known that some $O^*$ states such as singlet Oxygen have long life and can persist in liquids (Plasma Activated Media—PAMs, [2]) for significant times (the $1\Delta g$ singlet state is 0.9773 eV above the triplet $3\Sigma^-_g$ ground state.

There is ample evidence that RONS generated in CAPs are responsible for decolonization of bacteria and viruses as well as causing tumor cell apoptosis without affecting normal cells. Bauer et. al. [2] in particular, published a detailed article about the plasma interaction and the impact on cancer cell chemistry by demonstrating that tumor cell-generated RONS play a major role in inactivating protective catalase, depleting glutathione and by establishing apoptosis-inducing RONS signaling. CAP exposure triggers this response by initially inactivating a small percentage of protective membrane associated catalase molecules on tumor cells. Maisch [3] showed that CAP treatment of porcine skin lead to 5 log 10 reduction (99.999%) in MRSA while not affecting healthy skin cells. In Melanoma treatment with CAPS, similar selectivity has been observed [2].

Large area wound treatment using CAPs has been shown [4] to be a complex process involved with infection, cell proliferation/migration, and skin remodeling. For normal wounds, the first-stage inflammation occurs in 24-48 hr after tissue damage. Bacteria, neutrophils, and platelets are abundant with normal skin appendages present outside the wound. The second stage lasts from 2 to around 10 days, during which scabs form on the skin and cell migration and proliferation occurs. New blood vessels populate the wound area. Skin remodeling starts in the next stage and usually lasts a year or even longer. A scar is usually left, and the healed area does not contain normal skin appendages.

CAP treatment of wounds [5] has been shown to be effective because of CAPs ability to simultaneously kill bacteria and viruses while CAPs also have an effect on some fungi [6]. Wound repair is related to cell proliferation and migration as well as angiogenesis. Cell types involved in wound healing are mainly fibroblasts and keratinocytes, where the latter contribute to the major healing processes and former play a guiding role. It has already been reported that CAPs can increase fibroblast cell proliferation by using N2/Ar micro plasma through simulated release of fibroblast growth factor-7 [4].

DBD discharges are known to also produce Ozone and Ultra-Violet (UV) radiation, which is to some extent uncontrolled, and can have negative side effects. DBD sources have been around for many years and their effect on surface decontamination and use in medicine has been well documented [1] and most of the scientific literature around using plasmas in medicine is centered around DBDs simply because there are not many choices for atmospheric plasmas. DBDs typically use a high voltage (5-10 kV) and switching circuit operating at 1 to 35 kHz to create the breakdown voltages.

Standing Wave Plasmas as described herein on the other hand are microwave based and typically operated between 10 MHz and 10 GHz, although there is some indication that this range will extend to 20 GHz or more. The advantages of using microwaves, is that there is no discharge which means lower peak electron energy, lower UV and Ozone production and much better control over the RONS species that are actually generated in the plasma. User exposure to microwave radiation is expected to be similar to that from cell phones and in a similar frequency domain.

Using microwave frequencies allows a much tighter electron energy distribution so that process parameters can be dialed in-which we believe will result in a much better targeted killing of cells and bacteria. At microwave frequencies there is also significantly lower Ultra-Violet and Ozone exposure resulting in potentially less damage to healthy tissue and fewer side effects.

Waveguides and power supplies for microwave generation are easily available up to 2.45 GHz. Beyond that frequency waveguides are easily available, but power supplies are less common since they were developed primarily for low volume tele-communication and military market applications. However, the move to 5G Telecom amplifiers which uses similar frequencies, will make obtaining or developing a solid-state microwave power supply from 10 to 25 GHz certainly feasible.

The ability to create Multiple SWPs (MSWPs) simultaneously as described herein is a significant advantage because the linear nature of MSWPs and the much better control and lower UV generation should make MSWPs for the use in plasma treatment of cells, wounds etc. very interesting, particularly for large treatment areas. MSWPs generate similar plasma species as DBDs, with less UV and Ozone. Furthermore, because the MSWP has interchangeable plasma applicator capabilities, a dermatologist working with the system can easily select the correct plasma applicator for the particular patient, whether it is a single pencil shaped beam, or a MSWP.

Deposition technologies include physical vapor deposition (PVD), chemical vapor deposition (CVD) (either at atmospheric pressure (APCVD) or reduced pressure (LPCVD)), Atomic Layer Deposition (ALD), electroplating, evaporation, thermal flame spray, and thermal plasma spray. Many of these deposition technologies are used for the manufacture of materials layers such as semiconductors, carbon-nanotubes, industrial coatings, biomedical coatings, and the like. Oftentimes a balance has to be struck between technical concerns such as layer adhesion, contamination from undesirable elements, deposition rates, and uniformity (both on a global and on a microscopic scale), and commercial concerns such as the cost of performing such a deposition (materials costs and the effective use of the materials) as well as the cost of the manufacturing equipment deployed.

Ion implantation, including the extraction of ions from a plasma, is used to transport ions to a substrate with sufficient kinetic energy that the ion penetrates the surface sufficiently to become interspersed with the substrates' atoms. Ion implantation is both used for the modification of surface characteristics of the substrate such as hardening, as well as for interstitial doping of semiconductor materials thereby altering the substrate's electrical characteristics. Ion implantation is mostly done in a vacuum environment because the generation of an ion beam over sufficient distances requires an environment (a vacuum) wherein the ions do not neutralize by collision with other molecules or atoms, such as would be the case at atmospheric pressures.

Generally, processes that employ a vacuum or reduced pressure environment are subject to higher capital equipment costs and demonstrate lower deposition rates. However, the benefit of operating in a reduced pressure environment is often a reduction of contamination and an increase in uniformity and adhesion effectiveness. Furthermore, some processes may not work at all at higher pressures and therefore require a lower pressure or vacuum level operating regime.

Inductively Coupled Plasma (ICP) sources typically employ an electrical coil powered by radio frequency signal (around 1-13 MHz is common range of frequencies). The RF signal generates a rapidly changing electromagnetic field. This field can be coupled into a chamber to produce a plasma.

Electron Cyclotron Resonance (ECR) plasma sources are commonly used to support deposition chemistries for various materials. ECR sources combine a microwave source (typically operated between 1 and 10 GHZ) and a permanent- or electro-magnetic field, in which the microwave source supplies power to the plasma discharge region and where the magnetic field is responsible for the creation of helical paths for charged particles such as electrons and ions. Thus, because of the helical paths, the collision probability between charged particles and neutral particles is significantly increased, resulting in much longer residence times for the charged particles in the plasma region and an enhanced interaction time between the charged particles and other particles in the plasma. This enhanced residence time allows the charged particles (particularly the electrons) to create additional ionized particles in the plasma, resulting in much higher charge concentrations in the plasma region. These higher charge concentrations result in higher extraction rates of the desired particles. This is particularly useful in processes such as ion assisted deposition or in ion doping processes. Furthermore, the longer residence time of the electrons allows for an overall increase of the plasma temperature.

ECR plasmas are very common in the manufacturing of semiconductor devices. Most ECR plasma systems require vacuum levels well below atmosphere to be able to operate, and thus require expensive equipment. However, ECR phenomena have been observed at elevated pressures as well.

Plasma sources that deliberately enhance the formation of waves are Surface Wave Plasma sources (SWPs). They are also referred to as "Surfatrons." Surfatrons are plasma sources that are deliberately designed to create enhanced plasma wave operations. In general, SWP plasmas exhibit some unique characteristics such as the formation of (meta) stable surface waves along a boundary with an electrically insulating wall, wherein the plasma itself functions as the conductor so that plasma waves can be emitted over long distances away from their source of origin.

In accordance with one or more embodiments, methods and systems are provided wherein a waveguide receives microwaves from a source and transmits these microwaves through slots in the side of the waveguide that are sufficiently large to allow for the passage of the microwaves in a plane primarily perpendicular to the primary axis of the waveguide into a plasma chamber. In some embodiments, the waveguide has slots on one or more of its sides. In some embodiments, these slots are cut at an angle to the primary axis of the waveguide. In some embodiments, the angle between the primary axis of the waveguide and the main axis of the slots can range between 0 and 90 degrees. In some embodiments, the angle is cut at 45 degrees.

In accordance with one or more embodiments, methods and systems are provided wherein the waveguide is penetrated on a side opposite the slots by one or more pipes or tubes. In some embodiments, such pipes are constructed from metals or ceramics suitable for operation at elevated temperatures. In some embodiments, such pipes are used to transport materials across the microwave guide into the slots that lead to a plasma chamber. In other embodiments, each of the pipes contains different materials or combinations of materials.

In accordance with one or more embodiments, methods and systems are provided wherein the plasma chamber is equipped with permanent or electromagnets in order to allow for the creation of an Electron Cyclotron Resonance (ECR) effect. In some embodiments, the magnets have orientations suitable for the creation of high magnetic fields along the wall of the chamber and a substantially low magnetic field along the primary axis of the plasma chamber. In some embodiments, the magnets are permanent magnets. In some embodiments, the magnets are arranged in a logical pattern in between the microwave slots. In some embodiments, the magnets are arranged along an axis primarily parallel to the main axis of the plasma chamber. In some embodiments, the magnets are arranged at an angle to the main axis of the plasma chamber. In some embodiments, the magnets are arranged at an angle of 45 degrees to the main axis of the microwave chamber. In some embodiments, the magnets are mounted in cavities in the walls of the ECR chamber to keep them from being exposed to the plasma in the chamber. In some embodiments, the short walls of the ECR chamber are created to be primarily parallel to the microwave slots.

In accordance with one or more embodiments, methods and systems are provided wherein a waveguide receives microwave radiation from a source and wherein the waveguide has slots cut into one or more of its sides to allow the microwave radiation to enter an ECR plasma chamber and wherein there are pipes or tubes on the opposite side of the microwave slots to allow for the introduction of materials such as gasses, powders, liquids, solids or any combination of these. In some embodiments, the materials are mixes of materials. In some embodiments, the materials are powders that are coated with other materials so that the core of the powder has a lower melting temperature than the coating and so that the internal material melts away while in the plasma discharge region and thereby leaves a hollow shell that can be deposited on the substrate. In some embodiments, such pipes can be individually controlled as to how much material to introduce into such a plasma chamber and as to at what time. In some embodiments, the material is provided through the pipes in a pulsed fashion.

In accordance with one or more embodiments, methods and systems are provided wherein a waveguide receives microwave radiation from a source and wherein the waveguide has primary slots cut into one of its sides to allow the microwave radiation to exit the waveguide through appropriately sized slots and wherein the waveguide is terminated by a moveable first plunger, and wherein furthermore additional secondary slots are cut approximately equal in size to the first set of slots but located in the opposite wall of the waveguide. In some embodiments, such secondary slots are fitted with a secondary set of plungers called "ejectors." In some embodiments, such secondary sets of ejectors are used to create an amplification of the emitted radiation through the primary slots, resulting in a significant increase of emitted microwave power and an increase in the narrowness of the emitted microwaves beams. In some embodiments, such secondary plungers are used to optimally tune the emittance of each individual slot. In further embodiments, such secondary plungers are used to create a second standing microwave exiting the waveguide's primary openings. In some embodiments, the primary slots and the secondary plungers are used to emit radiation into a plasma chamber. In a further embodiment, such emitted radiation is used to create a surface wave plasma in the plasma chamber. In further embodiments, the emittance of surface wave plasma is used to impart momentum on a space vehicle. In yet another embodiment, the surface wave plasma is combined with a magnetic field to create both a surface wave plasma as well as an ECR plasma in the plasma chamber region.

Some plasma systems can be operated in atmospheric as well as under vacuum conditions. For medical applications, atmospheric operation (for example to treat a patient's skin) is generally required, although some medical samples have been processed under vacuum conditions as well. When treating patients in medical applications, keeping a much lower power level than for deposition or high-speed coating is generally more than adequate. Furthermore, the plasma outlet temperature generally needs to be tolerable to biological materials which means between 20 and 50 C. In medical plasma treatment, typical gases used for plasma generation comprise Argon or Helium carrier gases where either some Oxygen or Nitrogen is mixed in, or where some amount of air in the environment is added into the plasma column to generate RONS species as discussed earlier.

BRIEF SUMMARY

In accordance with various embodiments, plasma applicators are disclosed for the treatment of surfaces and liquids. In some embodiments the treated surfaces are skin surfaces. In some applications the treated skin surfaces are contaminated with viruses, bacteria, fungi, or other contaminants that can be selectively killed by plasma treatment. In some embodiments, the treated skin surfaces have cancerous growths such as melanomas, squamous- or basal-cell carcinomas, wounds or other defects. In some embodiments, the liquids treated by the plasma applicator are deionized- or regular- or Milli-Q water, saline solution, cell growth medium, Dulbecco's Modified Eagle Medium (DMEM), Basal Medium Eagle (BME), etc. In some embodiments, the plasma applicators comprise a waveguide supplied by a microwave power generator and a short (primary plunger) at the opposite end of where the microwaves are introduced. In some embodiments, the waveguide and short are sized so that a standing microwave is created inside the waveguide. In some embodiments a secondary ejector is placed in a set of first slots cut into the waveguide at locations where the standing microwave reaches maximum field levels. In some embodiments, the secondary ejectors comprise one or more ceramic, or glass pipes, a metallic sleeve around the pipe, and a secondary plunger around the sleeve. In some embodiments, the sleeve and pipe are inserted through the secondary plunger and into the waveguide to near a second slot cut into the wall of the waveguide on the opposite side of where the first slot is located. In some embodiments, the tube and/or metallic sleeve are close enough to the opposing slot in the opposite side of the waveguide to create a strong electromagnetic field in the gap between the sleeve end and the opposite opening to create a secondary standing microwave, which in turn generates a plasma inside the pipe or pipes. Such a microwave plasma is also known as a Surface Wave Plasma (SWP).

In some embodiments, the ceramic or glass pipe extends through the opposing waveguide wall whereas the metal sleeve surrounding the pipe is kept short of the wall inside the waveguide so as to create a small gap between the metal sleeve and the opposing wall. In some embodiments, the ceramic or glass pipe is terminated in a nozzle shaped tip, thereby allowing any gas that is injected into the tube to be pressurized and exit through the nozzle tip at a much lower temperature, and higher velocity by means of expansion of the gas. In some embodiments, the amount of gas cooling is approximately balanced by the amount of power that the secondary standing microwave injects into the created plasma, thereby creating a Cold Atmospheric Plasma (CAP) at approximately a temperature between 20 C and 50 C, suitable for interaction with human tissue, also known as a non-thermal plasma beyond the outlet of the nozzle.

In some embodiments, multiple ceramic or glass tubes with nozzle tips are provided to distribute the plasma over the surface such that a surface can be more evenly covered by the exiting plasma beams from the nozzle tips. In some embodiments the secondary ejectors are located on the waveguide centerline. In some embodiments the secondary ejectors are located at locations staggered along the main axis of the waveguide. In some embodiments the secondary ejectors are oblong. In some embodiments the oblong ejectors are oriented at an angle to the central axis of the waveguide. In some embodiments, the angles are alternating between the secondary ejectors, orienting one secondary ejector in a clockwise direction, and the second secondary ejector in a counterclockwise direction in relationship to the main axis of the waveguide.

In some embodiments, the plasma applicators described above can be connected using bend sections of waveguide, thereby connecting multiple applicators together in order to treat larger surfaces with the plasmas ejected by the applicators. In some embodiments such a connecting waveguide maintains the ability to create a primary standing microwave through the connecting sections of waveguide.

In some embodiments, the plasma applicator described above injects a surface wave plasma emanating from the ceramic tube into an ECR plasma chamber surrounded by magnets. In some embodiments, the plasma chamber generates a negative ion ECR plasma powered by the surface wave plasmas emanating from the ceramic tubes and the secondary ejectors. In some embodiments, the ECR plasma chamber has openings allowing negative ion species to be transported outside the ECR chamber. In some embodiments, the openings have an electrostatically charged extractor plate in close proximity with openings matching the plasma chamber openings, so that the negative ions can be actively extracted from the ECR plasma. In some embodiments, the thus extracted negative ions are directed toward a substrate. In some embodiments, the space between the extractor plate and the substrate contains a radiofrequency powered plasma region, generated by biasing the substrate using a radio frequency power supply.

In some embodiments, the gap between the sleeve and the bottom of the waveguide is outfitted with a coil as described in Paranjpe (U.S. Pat. No. 5,389,153). In some embodiments, an ignitor coil is located outside the waveguide, but in close proximity to where the ceramic tube exits the secondary slot in the waveguide. In some embodiments, the ignitor coil is wrapped around the ceramic tube. In some embodiments, the igniter coil is activated when a plasma inside the ceramic pipe needs to be started. In some embodiments, the igniter coil receives a high voltage pulse from a power supply. In some embodiments the power supply is controlled by a control system and program.

In some embodiments, a microwave is created inside a waveguide, wherein the microwave power entry is through a connector coupled to a small antenna structure located ¼ $\lambda_g$ away from an end of the waveguide. In some embodiments the antenna structure receives power from a microwave power supply and emits microwaves along the rectangular waveguide. In some embodiments the rectangular waveguide is terminated at the opposite end of the antenna structure by an electric, primary short. In some embodiments the short is fixedly located. In some embodiments, the short is movable. In some embodiments the distance between the antenna and the short is equal to $N*½\lambda_g+¼\lambda_g$, where N is a whole number equal to or larger than 1, and $\lambda_g$ is the wavelength of the microwaves inside the waveguide, thereby creating a standing microwave inside the waveguide. In some embodiments the antenna is located $¼\lambda_g$ away from the end of the waveguide.

In some embodiments, the waveguide is equipped with secondary ejectors. In some embodiments such secondary ejectors are located at maximum field strengths of the standing microwave inside the waveguide. In some embodiments, such secondary ejectors are circular, rectangular or oblong in cross section. In some embodiments, such secondary ejectors comprise one or more pipes, a metallic sleeve around such pipes, and a secondary plunger short around the metallic sleeve. In some embodiments the secondary plunger is fixedly located with respect to the metal sleeve. In some embodiments, the secondary plunger is located inside a metallic housing which is fixedly connected to the waveguide at a first slot cut into the waveguide wall. In some embodiments, the secondary ejector is mounted on a wide wall of the rectangular waveguide. In some embodiments, a second slot is cut in the wide wall opposite the ejector location. In some embodiments, the metal sleeve is extended around the pipe or pipes inside the waveguide to near the inner opposing wall and near the second slot. In some embodiments, the gap between the sleeve and the second slot is 0.1-5 mm. In some embodiments the gap is fixed. In some embodiments, the gap is adjustable by sliding the sleeve down closer to or up further away from the second slot thereby increasing or decreasing the field strength of the electric field between the sleeve and the waveguide wall surrounding the second slot. In some embodiments, the ceramic or glass pipe extents through the second slot beyond the waveguide wall. In some embodiments the pipe or pipes transports a gas or a mixture of gases. In some embodiments the gas is one or more of or a mixture of Argon, Helium, Oxygen, Nitrogen, Nitrous-Oxide or other gas species. In some embodiments, each of the pipes carries a different gas. In some embodiments, the gases flowing through the pipe or pipes are fed to a region through the gap between the sleeve and the wall where they become energized and a plasma is created inside the pipe or pipes. In some embodiments, the plasma is directed towards a surface. In some embodiments, the plasma is directed into an optional plasma diffuser chamber. In embodiment the plasma diffuser chamber receives multiple plasma beams from multiple secondary ejectors. In some embodiments, the plasma diffuser chamber is equipped with multiple outlet holes designed to evenly diffuse the created plasma species across a surface. In some embodiments, such a surface is a treatment area on a patient. In some embodiments, such a surface is a set of hands that need to be decontaminated from viruses, bacteria, fungi and the like. In some embodiments such a surface is the surface of medical instruments or apparatuses that need to be sterilized.

In some embodiments, that plasma applicator has plasma beams emanating from the secondary ejectors directly, or the plasma beams emanating from the optional plasma diffuser chamber, are directed towards or into a liquid medium, in order to create a plasma activated medium (PAM). In some embodiments such a liquid medium which can be one of deionized, or regular, or Milli-Q water, saline solution, cell growth medium such as Dulbecco's Modified Eagle Medium (DMEM), or Basal Medium Eagle (BME), etc.

In some embodiments, the plasma applicator has plasma beams emanating from the secondary ejectors directly, or the plasma beams emanating from the optional plasma diffuser, which are directed towards a stack of hollow membrane plates containing a liquid medium. In some embodiments such a liquid is a medium that can be one of deionized, or regular, or Milli-Q water, saline solution, cell growth medium such as Dulbecco's Modified Eagle Medium (DMEM), or Basal Medium Eagle (BME), etc., in order to create a PAM. In some embodiments the membranes are super-hydrophobic micro-porous membranes. In some embodiments, such membranes are made of a plastic material such as Polypropylene, Polyethylene, or any convenient material that allows easy exchange between the air/plasma medium on the one side and the liquid inside the membrane module on the other side. Common membrane materials are Celgard EZ9020 membrane made by Celgard LLC, which is primarily a Poly Propylene material or Solupor® 3P07A and similar variations thereof, manufactured by Lydall Solutech B.V. In some embodiments, the plasma beams emanating from the secondary ejectors or from the diffuser are outfitted with a turbulating structure so as to enhance the diffusion of plasma species through the membrane. Various examples of such turbulators are described for example in application U.S. 62/243,963 by Vandermeulen. In some embodiments, the hollow membrane plates have an internal structure that directs the liquid flow. In some embodiments, the structure directs the liquid to flow in a direction opposite to the plasma flow emanating from the plasma applicator.

In some embodiments, a plasma applicator is interchangeable with other plasma applicators. In some embodiments, one such plasma applicator contains a single, circular secondary ejector designed to create a narrow plasma beam. In some embodiments, another such plasma applicator contains a single, oblong secondary ejector designed to create a single ribbon beam. In some embodiments, yet another such plasma applicator contains multiple, oblong secondary ejectors designed to create a multiple ribbon beams. In some embodiments, the waveguide containing the one or more secondary ejectors is a flexible or curved waveguide. In some embodiments, yet another one of such plasma applicators is outfitted with a liquid bath. In some embodiments yet another one of such plasma applicators is outfitted with a membrane plate stack. In some embodiments the interchangeable plasma applicators are connected to a common power supply, a common control system, a common gas distribution system or all three, so that the high infrastructure cost of the power supply, control system and gas distribution system can support multiple plasma applicator configurations.

In some embodiments, the ceramic or glass pipe in the secondary injector is bent so as to exit the metallic sleeve inside the waveguide and is directed to a gas supply port in the waveguide wall. In some embodiments, the secondary plunger does not have a penetration for the glass or ceramic pipes, but rather is a single, short similar in function to the primary plunger. In some embodiments the primary or secondary plungers are fixedly connected to a motor, which can move the plunger upon a command from a controller. In some embodiments the controller receives input from a sensor system. In some embodiments the sensor system allows the controller to determine the proper plasma dose to apply to a treatment area or surface. In some embodiments, the controller also controls one or more gas supply lines allowing the controller to increase or decrease the flow of one or more gases through the one or more pipes. In some embodiments, the controller also controls an igniter near or around the one or more secondary ejectors in order to start a plasma column in the ceramic or glass pipes inside the secondary ejector. In some embodiments the ceramic or glass pipes are constructed as a Venturi nozzle, wherein a small amount of ambient air is inserted into the plasma region at a narrowed area ("waist") of the pipe by the relative vacuum created by the Venturi effect.

In some embodiments, the controller controls multiple secondary ejectors, multiple ignitors, multiple gases and one or more sensors or microwave power supplies simultaneously. In some embodiments, the secondary ejectors are located on opposite sides of the waveguide channel, thereby emitting plasma one two sides of the waveguide, and allowing for a more broad emission of plasma species in the surrounding environment.

In some embodiments, the secondary ejector comprises a secondary plunger fixedly connected to a motor and control system that can adjust the position of the secondary plunger to obtain power output tuning of the secondary standing microwave. In some embodiments, another motor is fixedly connected to the metal sleeve in the secondary ejector, thereby allowing adjustment of the gap between the metal sleeve and the output opening of the secondary ejector on the opposite wall of the waveguide. In some embodiments, the gap between the metal sleeve and opening on the opposite wall is covered by an electric insulator to prevent arcing between the metal sleeve and the waveguide wall across the gap.

In no way is the description of the applications of the present invention intended to limit the invention to these applications. In general, substantially any process that uses microwaves for the deposition of materials can benefit from the present invention.

DETAILED DESCRIPTION

Figure 1:
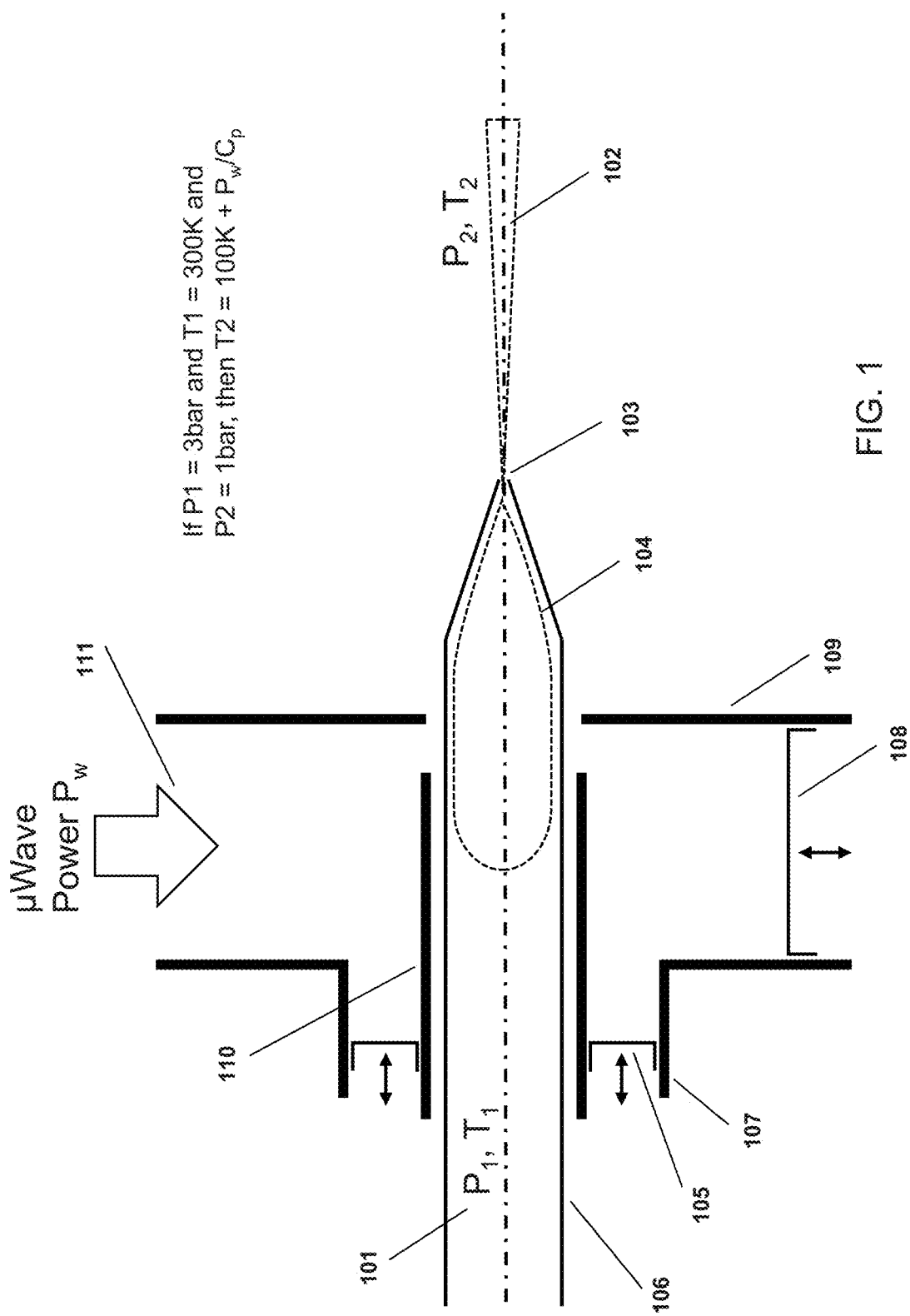
FIG. 1 shows an exemplary waveguide assembly in accordance with one or more embodiments showing a secondary ejector equipped with a narrowed tip in the ceramic or glass pipe.

FIG. 1 shows a waveguide assembly 109, which contains a primary plunger 108 opposite to the microwave inlet 111. The waveguide assembly 109 contains one or more secondary ejectors comprising of ceramic or glass or some other suitably electrically insulating pipes 106, metal or some other suitably conductive sleeve 110, a secondary plunger 105, and conductive or coaxial housing 107, have been equipped with tapered tips 103 at the end of the ceramic or glass pipes 106. In some applications, such as medical plasma applications, it is desirable to operate the plasma source at low power levels, thereby creating a Cold Atmospheric Plasma (CAP). CAPs are useful in applications in atmosphere for treating skin surfaces and other parts of the body, where the plasma temperature has to be maintained close to room temperature. Lower power levels leave the bulk gas temperature near room temperature, but the electron temperature of the plasma stays much higher (also called a non-Thermal Plasma). At very low power levels the plasma column 104 can become unstable or extinguish. Adding a tapered end nozzle 103 to the pipe 106 creates a higher gas pressure in the pipe which then expands into the surrounding atmosphere resulting in a lower pressure and temperature plasma 102 which then reduces the bulk gas temperature adiabatically, while maintaining the high electron temperature.

FIG. 1 furthermore illustrates a cross sectional view with an outline of the ejected plasma 102. Gas 101 enters under pressure $P_1$, and temperature $T_1$, typically 300K (about room temperature). By adiabatic expansion through nozzle 103, the exiting plasma column 102 will have a much lower temperature, which will be increased by the power $P_w$ added into the plasma by the microwave. This will allow for significant cooling of the bulk plasma, allowing the plasma to operate at higher power levels than would otherwise be possible, thereby also generating higher quantities of reactive plasma species such as Reactive Oxygen and Nitrogen Species (known as RONS). RONS are known to be beneficial in the treatment of skin cancers, help in wound healing and can selectively kill bacteria and viruses on surfaces. Keeping a much lower bulk gas temperature in plasma column 102 will therefor allow for the treatment of surfaces that cannot be exposed to high temperature gases such as human skin.

Figure 2:
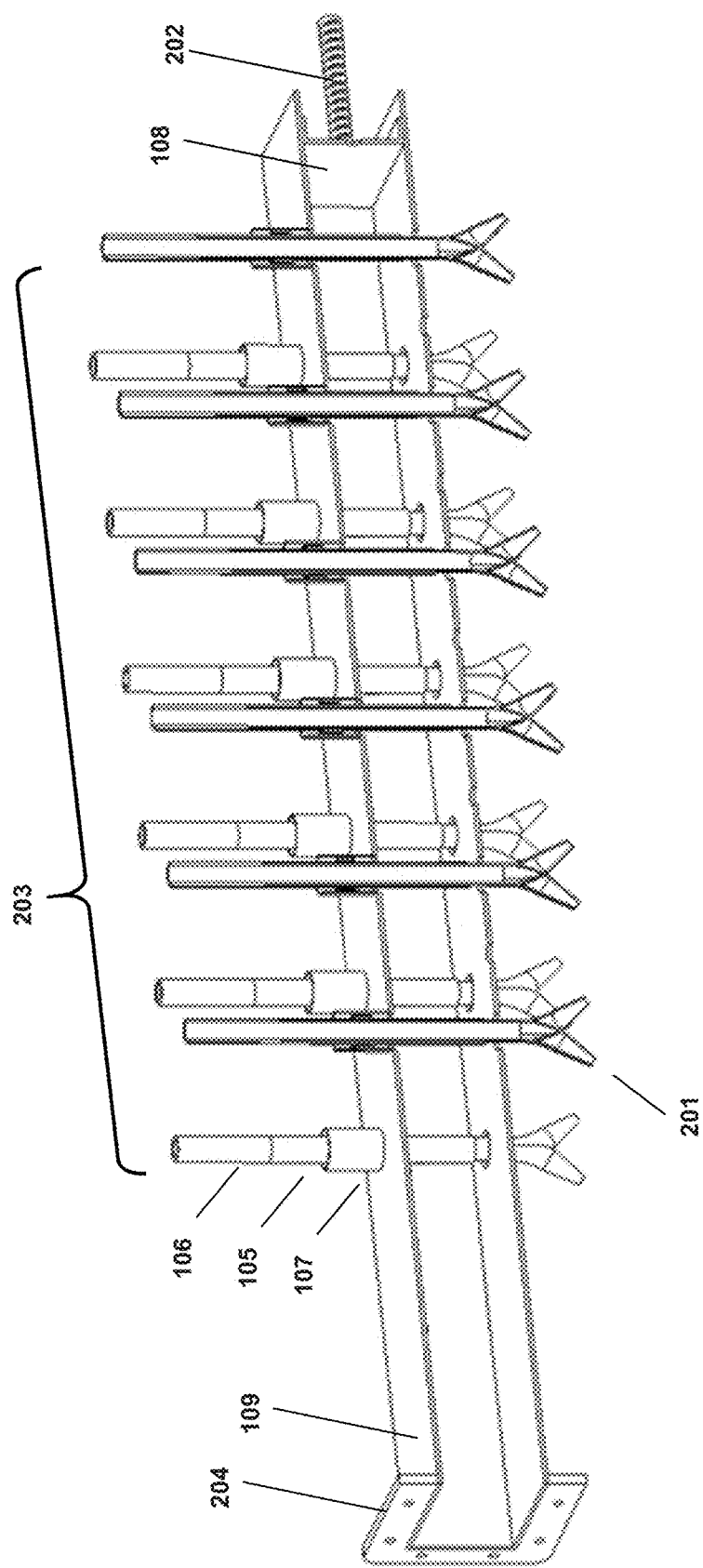
FIG. 2 is a cross sectional view of an exemplary waveguide assembly in accordance with one or more embodiments showing an array of secondary ejectors shown in FIG. 1 in a staggered alignment along a centerline of the waveguide conduit.

FIG. 2 illustrates a cross sectional view of an alternate embodiment of the narrowed pipes 106 of FIG. 1 wherein the pipe outlet 201 comprises multiple outlets and wherein the secondary ejectors 203 are located in a staggered pattern along the waveguide. The cross-section shown in the figure is cut through one set of secondary ejectors, and not on the centerline of the waveguide 109. By using staggered ejectors and employing multiple outlets on the ceramic pipes 201, a plasma blanket can be created below the surface of the waveguide 109. The figure furthermore illustrates a screw adjuster 202 and microwave inlet flange 204, which are discussed in more detail in, for example, U.S. Pat. No. 10,861,667.

Figure 3:
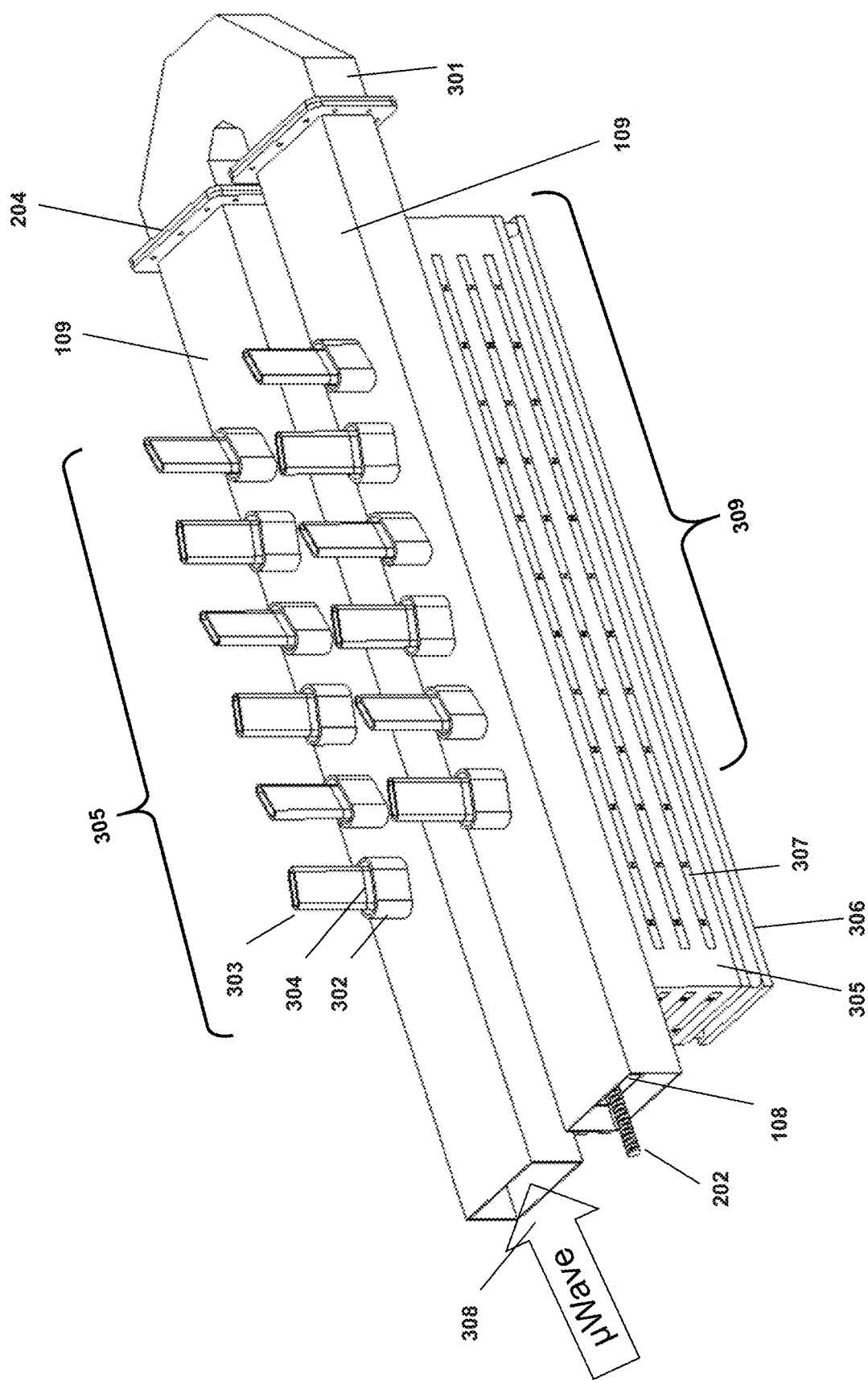
FIG. 3 illustrates an exemplary alternate waveguide assembly in accordance with one or more embodiments in which the secondary ejectors are located at alternating angles to the waveguide centerline and in which two sections of waveguide with their ejectors are connected through a bend section of waveguide, allowing for a more uniform surface treatment.

FIG. 3 illustrates an alternate embodiment of the secondary ejectors 305 similar to the oblong ejectors shown in U.S. Pat. No. 10,861,667. The ejectors in FIG. 3 have an oblong coaxial housing 302, a conductive sleeve 304 and an insulating oblong pipe 303. The ejectors 305 are located at alternating angles to the main waveguide centerline and wherein two sections 109 of waveguide with their ejectors 305 are connected through a U-shaped bend section 301 of waveguide, allowing for a more uniform surface treatment. It should be obvious that additional sections 301 and waveguide sections 109 can be added to create a plasma treatment system for larger surfaces. The figure also shows an optional ECR chamber 305, with magnets 307 installed on the walls of the ECR chamber and an extractor plate 306. Microwaves enter the inlet 308 are conducted through the first set of secondary ejectors 305, are conducted through the U-shaped connector 301 into a second set of secondary ejectors 309 and primary plunger 108 now helps created a standing microwave in both sections of the secondary ejectors.

Figure 4:
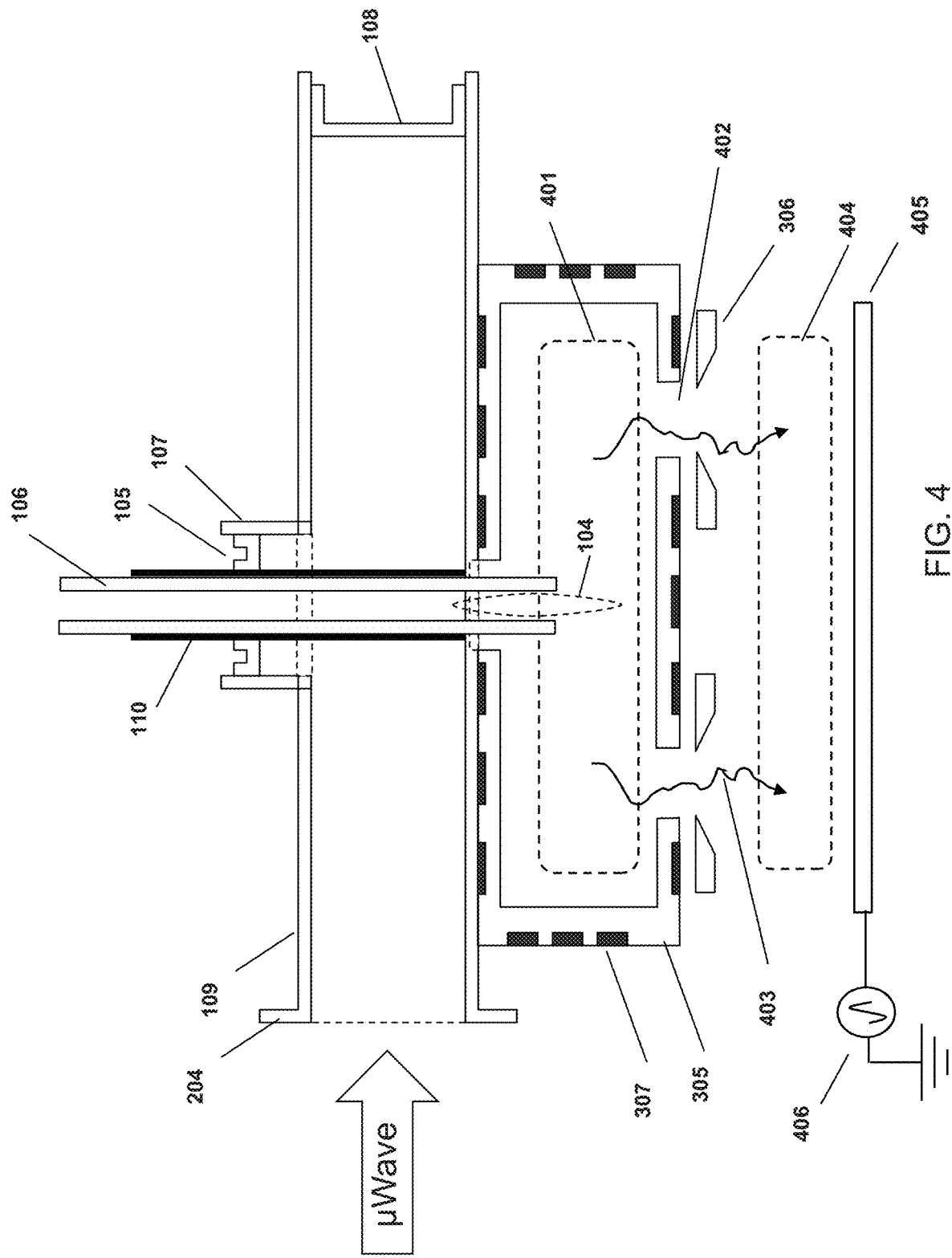
FIG. 4 illustrates an exemplary alternate waveguide assembly in accordance with one or more embodiments in which negative ions that are generated in the ECR plasma chamber are subsequently transported to a secondary plasma region.

FIG. 4 illustrates an alternative embodiment of FIG. 3. The plasma column 104 exiting from the secondary ejector region is used to create an ECR plasma 401 as discussed previously. The ECR plasma 401 is confined by magnets 307. This ECR plasma will contain a certain amount of negative ions 403, which can be extracted from the plasma by positively charging extractor plates 306 or by allowing negative ions 403 to drift through openings 402 in the ECR chamber 305. The negative ions 403 are directed towards a secondary plasma 404, which is generated by, for example, a radio frequency power source 406, similar to the plasma source described by Keller (U.S. Pat. No. 5,783,102). Keller however, generates the upper plasma 401 by using a Radio Frequency source, rather than a much higher intensity secondary standing wave as described here. Species generated in the secondary plasma 404 can be directed towards substrate 405, which is biased by the power supply 406. In this construction, a significantly higher amount of negative ions can be delivered to the substrate 405 or directed to an ion accelerator column instead of being directed to a substrate 405.

Figure 5:
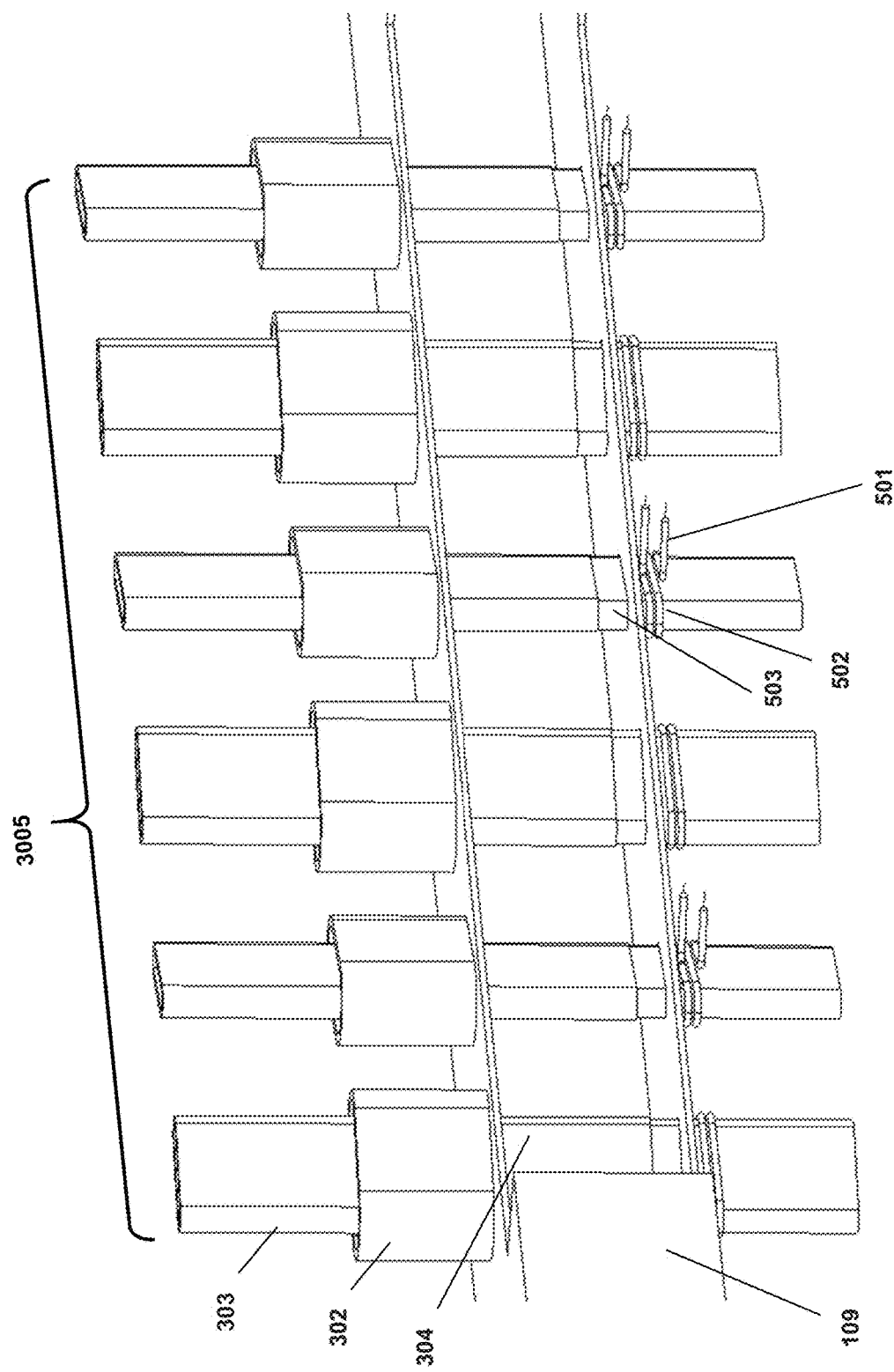
FIG. 5 illustrates an exemplary alternate waveguide assembly in accordance with one or more embodiments in which an ignitor coil is provided near the plasma generating region of the ceramic pipe exiting the waveguide.

FIG. 5 shows a section of an alternative embodiment of the secondary ejectors in FIG. 3, with a small section of the waveguide wall 109 removed for clarity and wherein an ignitor coil 502 has been placed near the plasma generating region 503 of the ceramic pipes 303 exiting the waveguide 109. At low required power levels as described above, it may be difficult to sustain the plasma, but even more difficult to get it started. Coils can be installed as shown in Paranjpe (U.S. Pat. No. 5,389,153), but ignitor coils 502 can alternatively be located near the plasma region 503. The advantage of this arrangement over Paranjpe is that the coils 502 can be activated by an electronic pulse through the wire leads 501, thereby igniting the plasma, even at relatively low power levels. This also means that in some cases the metal sleeve 304 can be fixed in position, eliminating the need to adjust the gap between the metal sleeve 304 and the bottom of the waveguide 109, in the plasma generating region 503, thereby simplifying the system.

Figure 6:
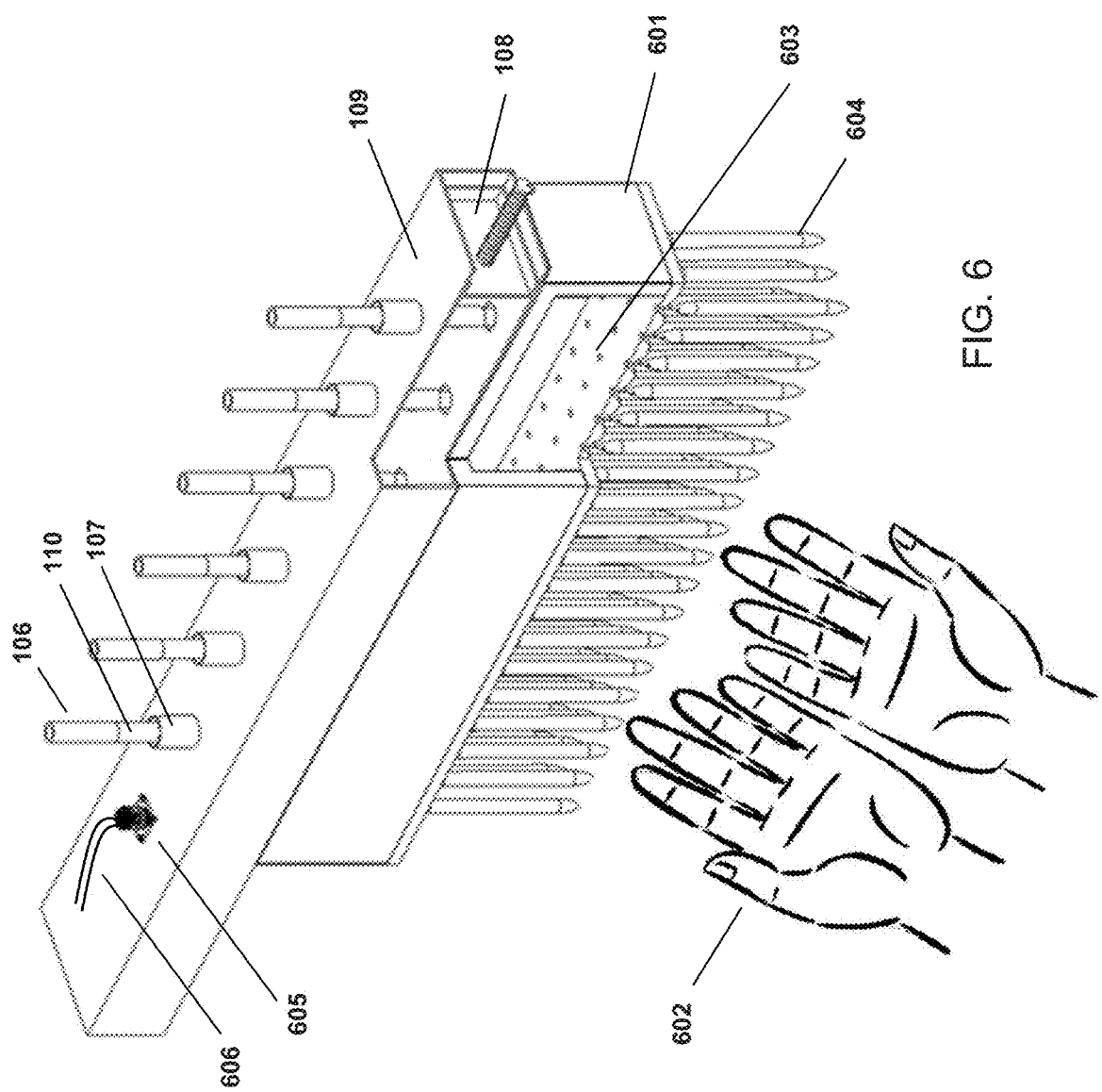
FIG. 6 illustrates an exemplary plasma applicator in accordance with one or more embodiments in which a number of plasma beams are directed towards a surface to provide disinfecting or healing properties of the plasma to the surface.

FIG. 6 illustrates a plasma applicator wherein a number of (RONS) plasma beamlets 604 are directed towards a surface 602 in order to provide disinfecting or healing properties of the plasma to the surface 602. As discussed above, RONS generated in plasma beams are known to have beneficial effects on skin cancers, selectively killing the cancer cells. RONS also kill viruses and bacteria on surfaces. In order to safely treat biological surfaces, the bulk plasma temperature needs to be kept low enough that such a treatment can be tolerated. FIG. 6 uses the nozzles from FIG. 1 to inject multiple plasma beams into an optional plasma diffuser chamber 601. Outlet holes in the diffuser 603 generate small plasma beamlets 604 from the diffuser 603, thereby allowing a surface 602 to be treated while maintaining a plasma temperature relatively close to room or body temperature. It should be clear that such a plasma applicator can be used as a "dry" method of disinfecting human hands, or skin because the RONS will selectively and rapidly kill any bacteria or viruses present on the surface 602.

FIG. 6 also shows that microwaves can be inserted into the waveguide 109 through a coupler 605, rather than through a flange 204 as shown in earlier figures. In low power (less than about 500 W) applications, a cable 606 can deliver the microwave power to the applicator. Microwave cables have practical limits on how much power can be transported from the power supply to the applicator, so for high power applications, a flange 204 to a microwave head such as a magnetron or klystron is more common.

Figure 7B:
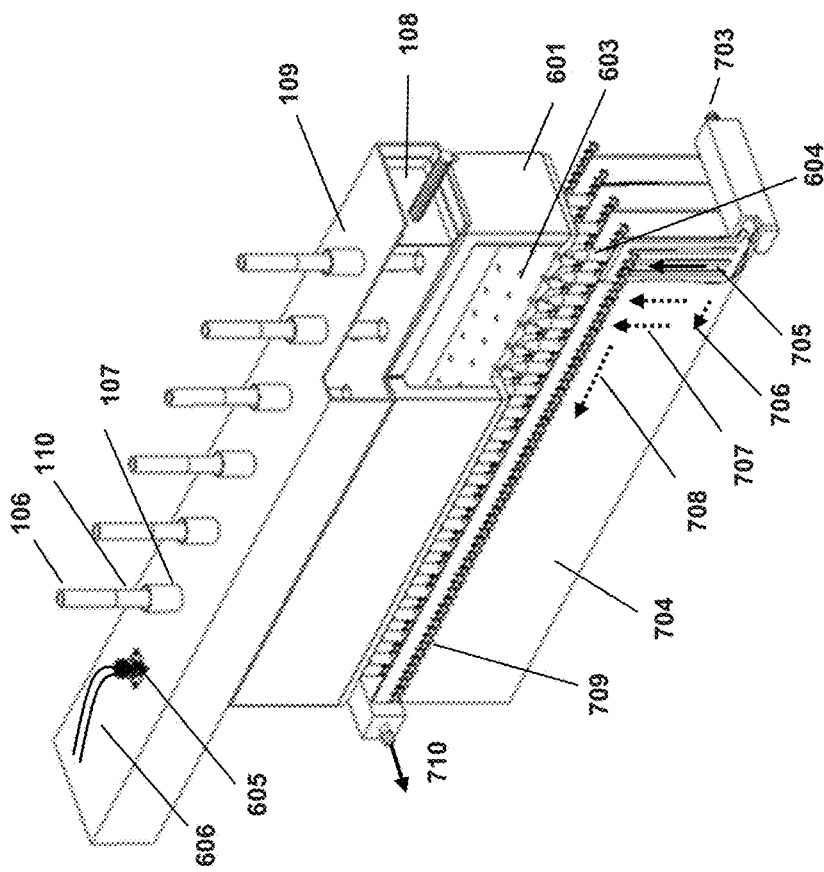
FIG. 7B shows the applicator of FIG. 7A, wherein the number of plasma beams are directed toward a set of hollow membrane plates containing a medium such as water, saline solution etc.
Figure 7A:
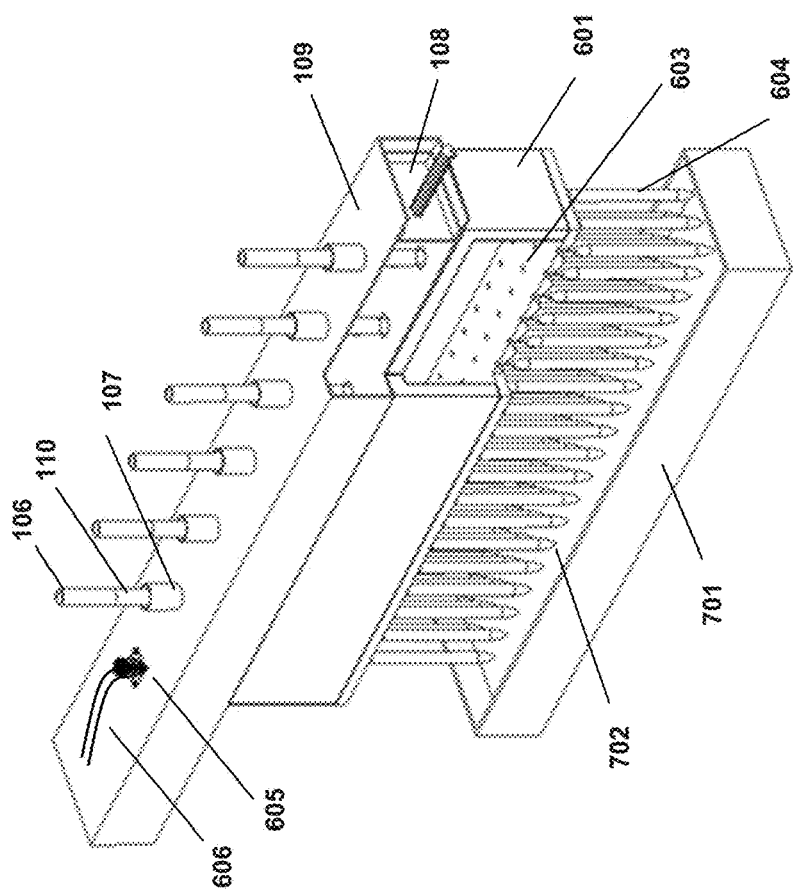
FIG. 7A shows the applicator of FIG. 6, wherein the number of plasma beams are directed towards a medium such as water, saline solution etc.

FIG. 7A shows the applicator of FIG. 6, wherein the number of plasma beams 604 are directed towards a liquid medium 702 contained in a container 701. Such a medium can be deionized or regular or Milli-Q water, saline solution, cell growth medium Dulbecco's Modified Eagle Medium (DMEM), Basal Medium Eagle (BME), etc. The plasma generated RONS, or Reactive Oxygen Species (ROS) or Reactive Nitrogen Species (RNS) 604, are directed towards or bubbled into the medium 702, thereby creating reactive plasma species in the medium also known as Plasma Activated Media (PAM). PAMs can be injected into cancerous tumors or other tissues, where they retain the ability to selectively destroy cancer cells, kill viruses or bacteria etc. for a period of several hours.

FIG. 7B shows the applicator of FIG. 6, wherein the number of plasma beams 604 are directed toward a series of hollow membrane plates 704 containing a PAM medium such as water, saline solution, DMEM, BME, blood, blood plasma, etc. In many cases such as in the case of blood, direct exposure of the medium to air might bring in undesirable contamination or oxidation. By directing the plasma beams 604 in between the member plates 704, and by adding optional turbulators structures 709, the medium behind the membranes can be exposed to the plasma beams 604 without being directly exposed to air. Also the membrane plates 704 create a significantly larger exposure area for the plasma and the medium to interact thereby enhancing the amount of medium that absorbs the plasma species. Medium is directed into port 703, where it gets distributed to each of the membrane plates 704. In this example, the membrane plate stack is set up as a counterflow medium-to-plasma exchanger. Medium 705 flows horizontally 706 along the bottom inside the membrane plates 704 and is then directed vertical channels 707 inside the membrane plates 704. When the medium 705 reaches the top of the plates 704 it flows along horizontal channels 708 until it reaches the exit port 710.

Figure 7C:
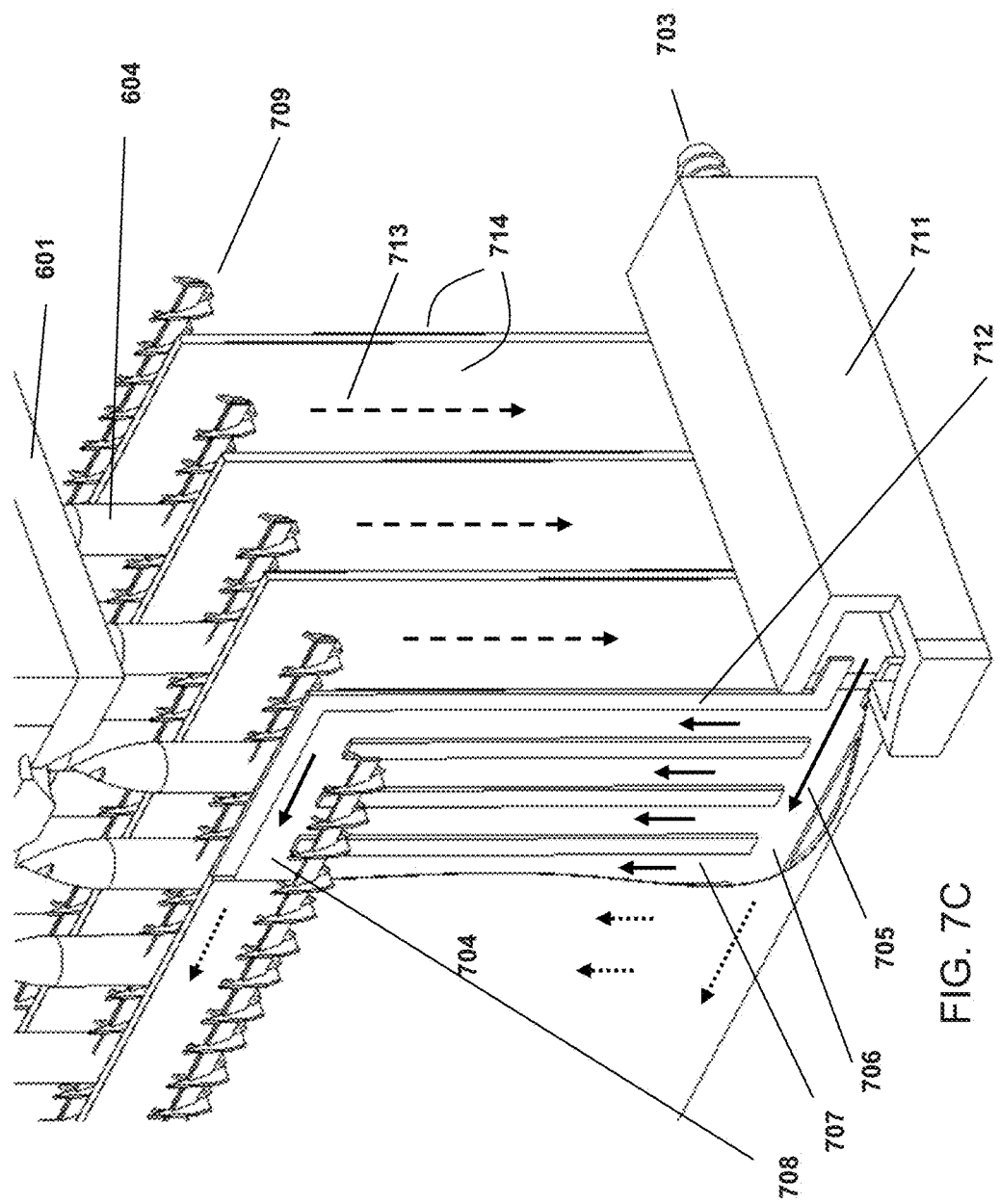
FIG. 7C shows a detail of the membrane plate assembly of FIG. 7B.

FIG. 7C shows a detail of the membrane plate assembly of FIG. 7B, wherein a section of the membranes 714 of the first membrane plate 704 has been removed to show the medium 705 flow patterns inside the plate 704. Medium 705 enters through port 703 and flows through distribution bulkhead channel 711 into the individual membrane plates 704. Each hollow membrane plate 704 is typically constructed with a support frame 712 which defines flow channels for the medium 705. The frame 712 is typically covered on both sides with a membrane 714, which can be a superhydrophobic membrane or some other suitable membrane. Plasma beams 604 are typically directed 713 against the flow of the medium 705 inside the membrane plates 704. Optional turbulators 709 can create vortex flows thereby enhancing the interchange between the plasma 604 and the medium 705, but preventing direct exposure of the medium 705 to the plasma/air stream. RONS in the plasma beams 604 will diffuse through the membrane 714 into the medium 705, thereby activating the medium 705 and potentially killing pathogens in the medium 705 such as viruses and bacteria. If the medium 705 is blood or a blood plasma, or saline, the thus activated medium 705 could be injected into a patient, for example into a patient suffering from a blood cancer or sepsis.

Figure 8A:
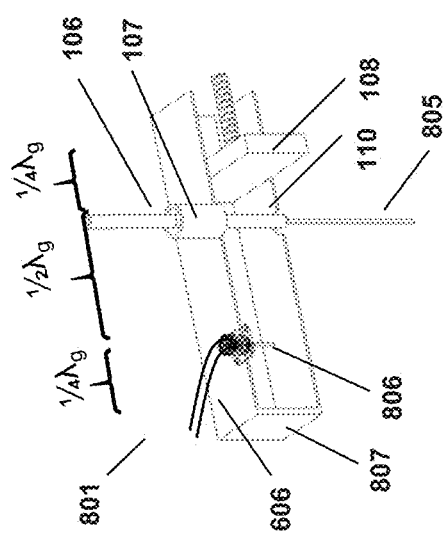
FIG. 8A shows an exemplary interchangeable plasma applicator in accordance with one or more embodiments with a single point beam.

FIGS. 8A through 8D show a cross sectional model of a set of interchangeable plasma applicators. FIG. 8A shows an applicator 801 with a single point beam 805. In some applications such as treating a small skin carcinoma, a small circular RONS plasma beam is easiest to use to treat a patient. Because the microwave connector 806 can be made common between all plasma applicators shown in these figures, it is possible to manufacture interchangeable plasma applicators that can be exchanged depending on the needs of the area to be treated. The microwave input 806 is kept at the same distance from the connector 806 to the first secondary ejector at ½ of the wavelength of the microwaves used and also is kept at the same distance to the waveguide wall 807. (typically ¼ of the wavelength of the microwaves used)). A variable power solid state microwave supply can typically deliver power between 2% and 100% of maximum power and therefore a wide range of applicators can share a single power supply.

Figure 8B:
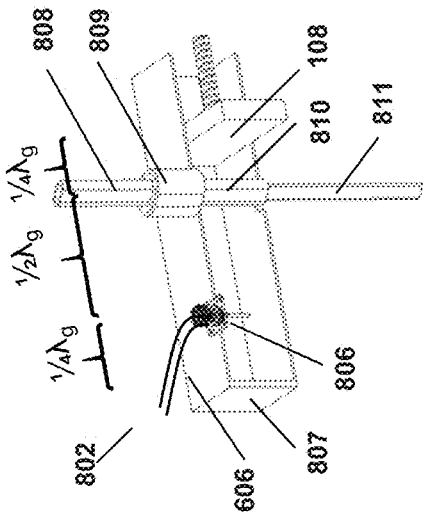
FIG. 8B shows an exemplary interchangeable plasma applicator in accordance with one or more embodiments with a single ribbon shaped plasma beam from an oblong ejector.

FIG. 8B shows a cut-through of an alternate embodiment of an interchangeable plasma applicator 802 with a single ribbon shaped plasma beam 811 emanating from an oblong ejector comprising an electrically insulating pipe 808, a metal sleeve 810 and a housing 809 as described earlier in FIG. 3. A small single ribbon beam 811 can be used to treat larger areas than the point beam of FIG. 8A.

Figure 8C:
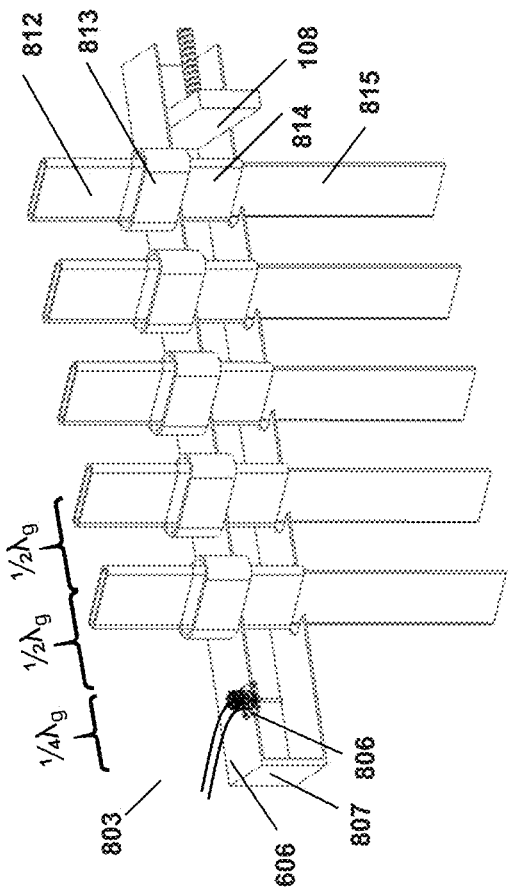
FIG. 8C shows an exemplary interchangeable plasma applicator in accordance with one or more embodiments with multiple ribbon shaped plasma beams to treat a flat surface.

FIG. 8C shows a cut-through of an alternate embodiment of an interchangeable plasma applicator 803 with multiple ribbon shaped plasma beams 815 to treat a large flat surface, for example such as treating a wall, a floor or any flat surface The large oblong secondary ejectors comprise multiple insulating pipes 812, housings 813 and metal sleeves 814.

Figure 8D:
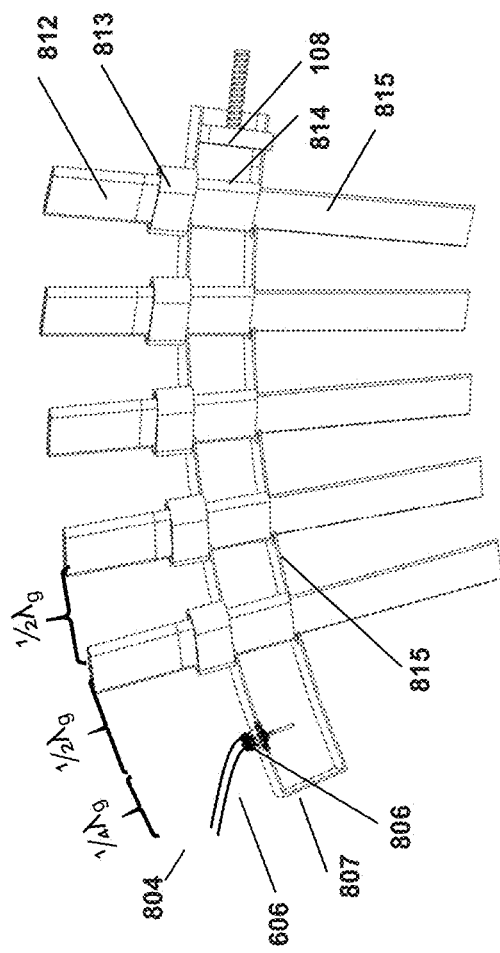
FIG. 8D shows an exemplary interchangeable plasma applicator in accordance with one or more embodiments with multiple ribbon shaped plasma beams on a flexible waveguide to treat a curved surface.

FIG. 8D shows a cut-through of an alternative embodiment of an interchangeable plasma applicator 804 with multiple ribbon shaped plasma beams 815 on a flexible waveguide 815 to treat a curved surface, such as for example a human leg, head or other curved surface.

It should be obvious that many different plasma applicators can be attached through a common microwave cable 606 and gas supply source. For example, it would be relatively easy to supply a dermatologist or hospital with a set of applicators for different skin surface areas as well as with a plasma activating medium applicator as was shown in FIG. 7A, FIG. 7B and FIG. 7C, thereby allowing for great treatment flexibility for both skin cancers as well of solid and blood cancers, all by using interchangeable plasma applicators and a common microwave power source and gas supply system, thereby significantly reducing capital costs.

Figure 9:
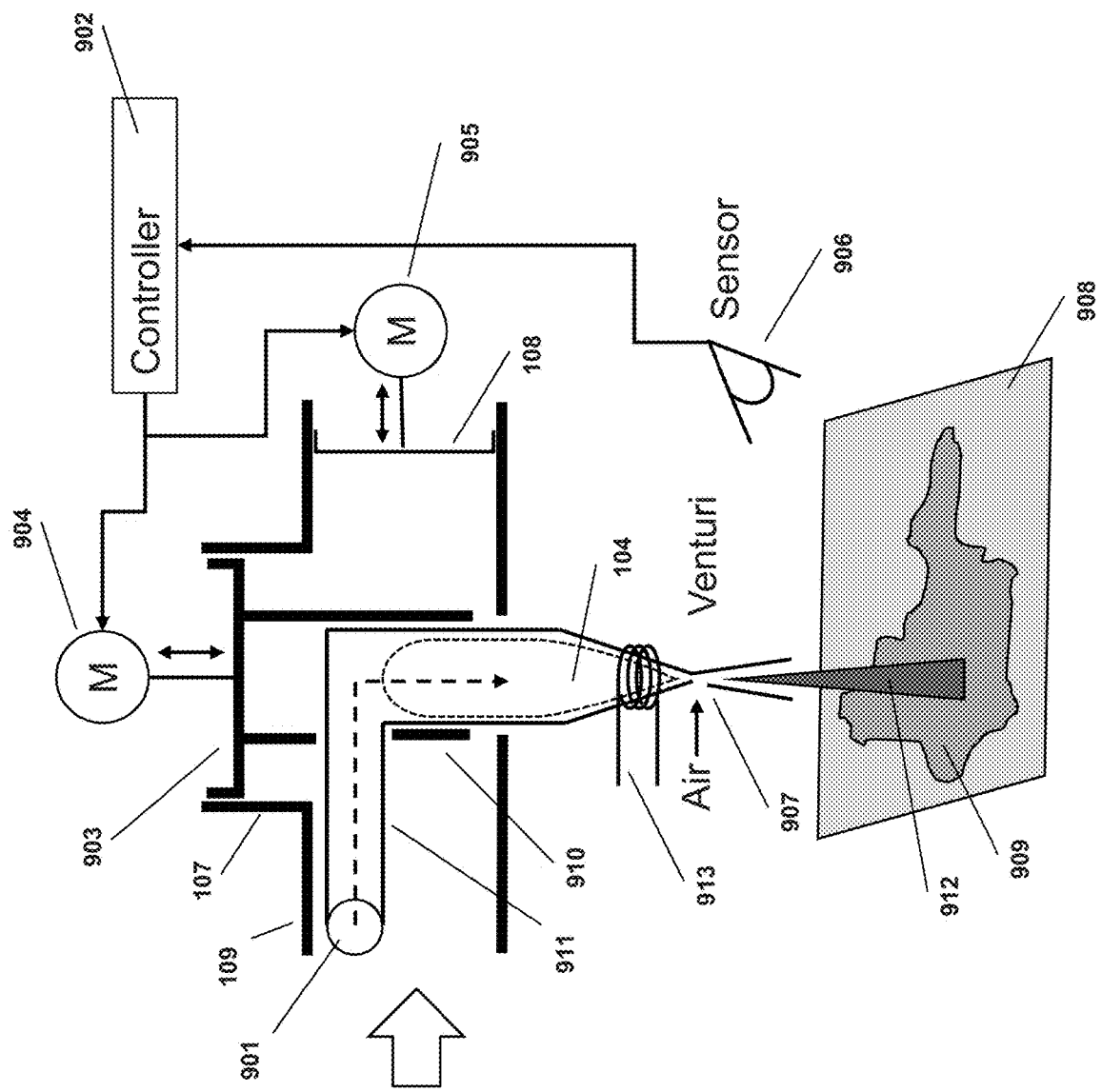
FIG. 9 shows an exemplary alternative embodiment of the secondary ejector with a side gas input port and controller for tuning the waveguide plungers, an ignitor coil, a Venturi nozzle, and a sensor to detect the proper dose of plasma to be applied to the surface, wherein a control system can be used for the plasma applicators in FIG. 7A-B and FIG. 8A-D.

FIG. 9 shows an alternative embodiment of the secondary ejectors shown in previous figures with a side gas input port 901 and a controller 902 for tuning the waveguide plungers 108 and 903 using motors 905 and 904, respectively. The controller 902 can also take sensor 906 data to compute a plasma dose to be applied to a substrate 908 so that the plasma beam 912 is properly covering the treatment area 909 and not needlessly treating the remaining area of substrate 908. Such a control system is convenient in the case where a RONS plasma is treating a larger cancerous area such as a melanoma or other surface cancer. The sensor 906 can be an optical sensor, a camera, a LIDAR (Light Detection and Ranging), RADAR (Radio Detection and Ranging), a spectrometer or any other convenient sensor that imparts surface density information and or plasma composition information to the controller 902. In the embodiment of FIG. 9, the secondary plunger 903 (e.g., secondary plunger 105 in FIG. 1) has been modified so that no ceramic pipe goes through the center of the secondary plunger thereby increasing the microwave reflecting area of the secondary plunger. Sleeve 910 has likewise been modified to allow for passage of gas pipe 911 into the plasma region 104. An ignitor coil 913 gives the controller 902 another means of starting the plasma 104. A Venturi nozzle 907 allows a small amount of air to be inserted into the plasma beam 912 thereby reducing the need for multiple gases or gas mixtures supplied through the gas pipe 901. The controller 902 thus has several means of controlling the dose of plasma to be applied to the treatment area 909: by moving the position of secondary or primary plungers a different plasma excitation mode or power level can be obtained. By controlling, or shutting of the gas supply to one or more ejectors, the plasma columns can be stopped temporarily and by using the ignitor coils 913 the local plasma beam 912 can be restarted when needed. The controller 902 can also change the gas mixture for example in a RONS mixture of 96% Argon, 2% Oxygen and 2% Nitrogen, the Oxygen or Nitrogen gas or both could be temporarily shut of thereby changing the RONS concentrations in a controlled fashion.

Figure 10:
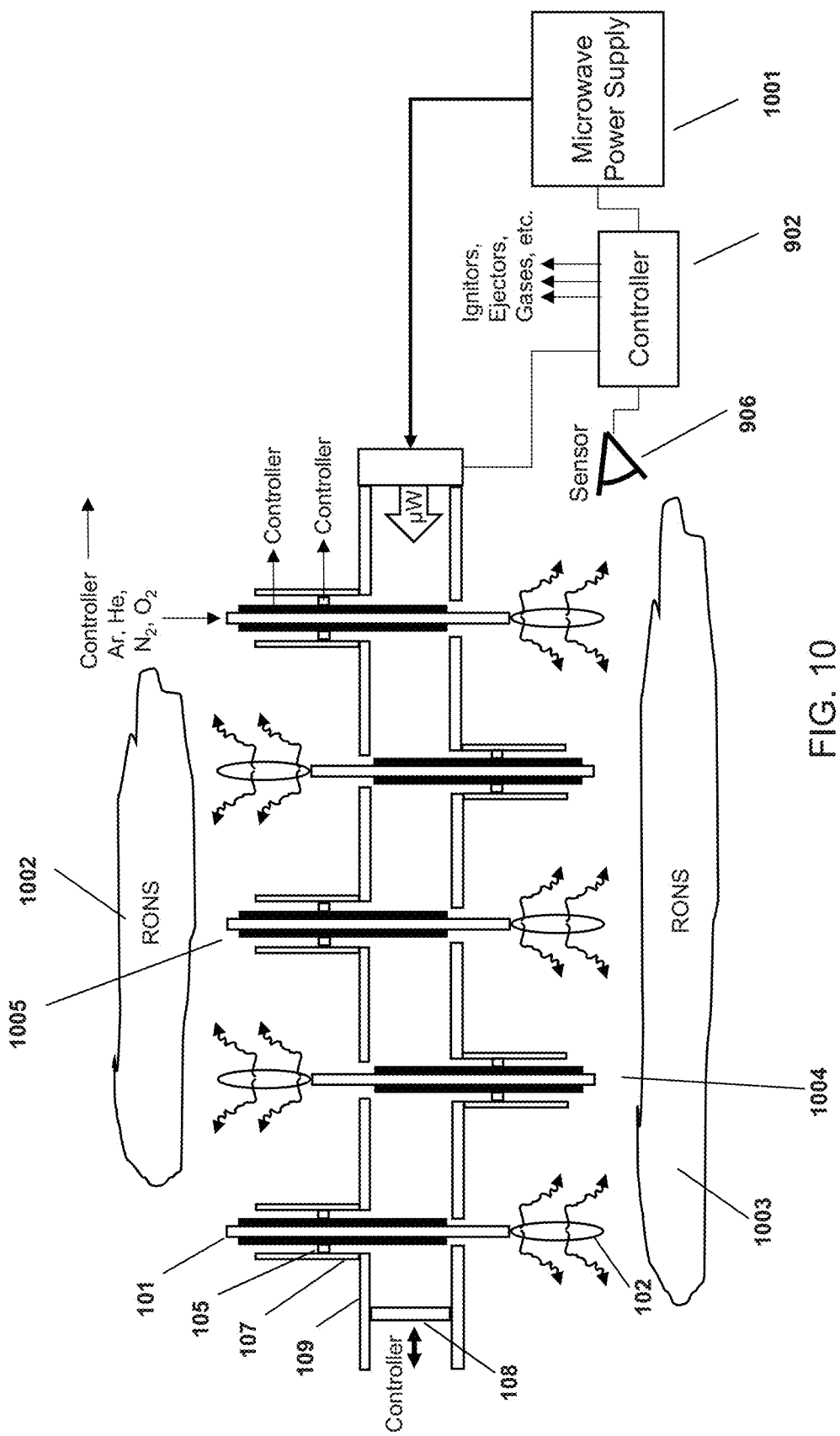
FIG. 10 illustrates an exemplary alternate embodiment of the secondary plasma ejectors, wherein ejectors are alternatingly located on opposite sides of the waveguide, thereby allowing for ejection of plasma species on two side of the waveguide, such as for the creation of RONS for treatment and disinfection of air. The figure also shows a simplified control system for an interchangeable plasma applicator system.

FIG. 10 illustrates an alternate embodiment of the system of FIG. 1, wherein alternating ejectors are located on opposite sides of the waveguide 109. By alternating the ejectors two separate RONS areas 1002 and 1003 can created on opposite sides of the waveguide. FIG. 10 also illustrates a simplified control system for the interchangeable, multi-ejector plasma applicator system shown in FIG. 7A through 7D, wherein the controller 902 can be used for the plasma applicators in FIG. 7A-B and FIG. 8A-D and simultaneously controls the microwave power supply 1001. Sensor 906 provides information to the controller 902 so that proper plasma dose can be applied to the treatment surface area. It should be clear that not all control elements of FIG. 10 are needed at all times. Several of the movable components may be fixedly located to reduce cost or complexity.

Figure 11:
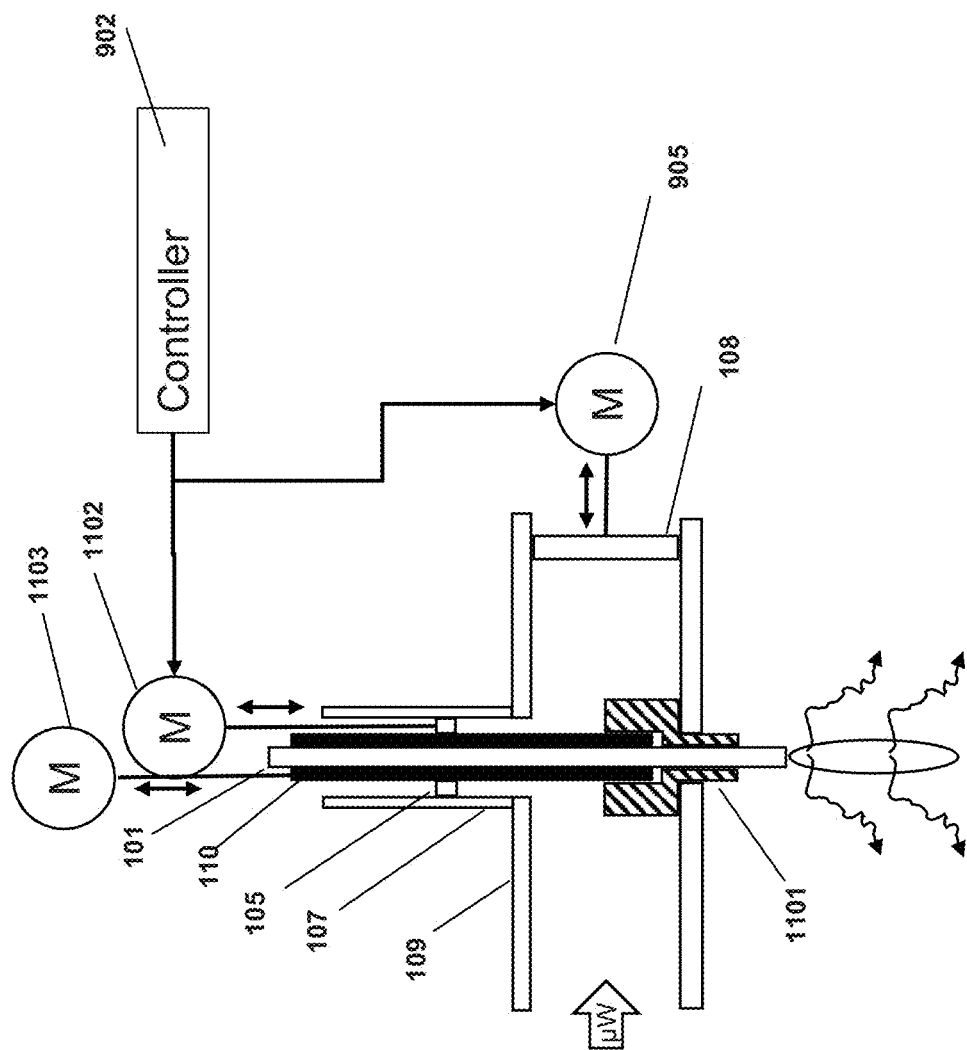
FIG. 11 illustrates an exemplary control system and a set of motors in accordance with one or more embodiments to move the primary and secondary plungers as well as the metal sleeve. Also shown in the figure is an insulator in the gap between the metal sleeve and the waveguide wall to prevent or inhibit arcing.
Figure 12:
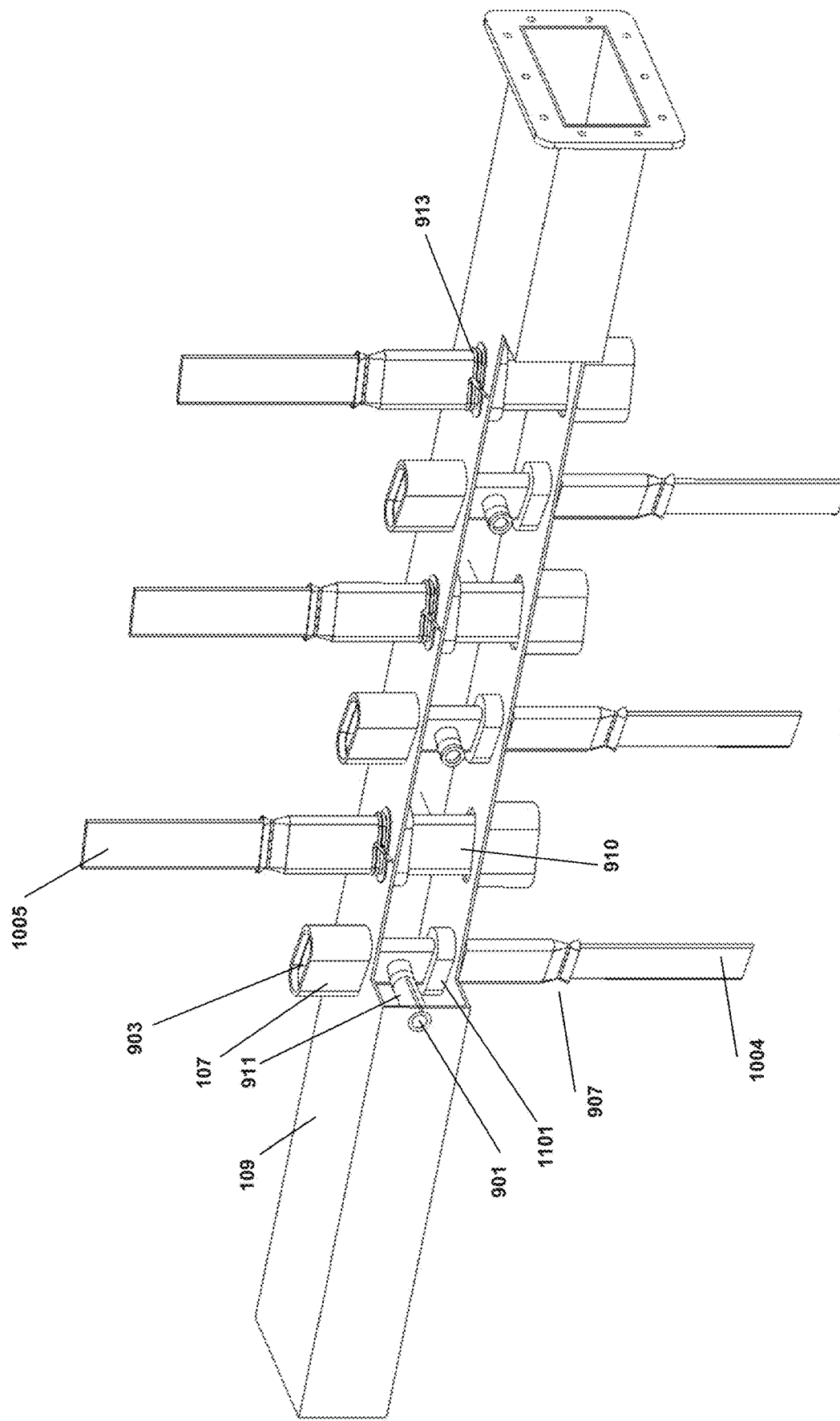
FIG. 12 shows a three dimensional view an exemplary plasma applicator in accordance with one or more embodiments with a section removed to illustrate various waveguide concepts of FIGS. 1, 5, 9, and 10.

FIG. 11 illustrates a spark prevention solution, which can be useful in applications where the electrical field strength in the gap between the metal sleeve 110 and the waveguide wall 109, can result in arcing, such as under high output power conditions. The insulating insert 1101 has a higher dielectric coefficient than a normal air gap, thereby making it harder for arcing to occur. The figure also illustrates a set of motors to control the primary plunger 108 with motor 905, the secondary plunger 105 through motor 1102, and the metal sleeve 110, through motor 1103.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

REFERENCES

[1] M. Izadjoo, S. Zack, H. Kim, and J. Skiba, "Medical applications of cold atmospheric plasma: State of the science," J. Wound Care, vol. 27, no. Sup9, pp. S4-S10, September 2018, doi: 10.12968/jowc.2018.27.Sup9.S4.

[2] G. Bauer, D. Sersenová, D. B. Graves, and Z. Machala, "Cold Atmospheric Plasma and Plasma-Activated Medium Trigger RONS-Based Tumor Cell Apoptosis," Sci. Rep., vol. 9, no. 1, pp. 1-28, 2019, doi: 10.1038/s41598-019-50291-0.

[3] T. Maisch et al., "Decolonisation of MRSA, S. aureus and E. coli by cold-atmospheric plasma using a porcine skin model in vitro," PLOS One, vol. 7, no. 4, pp. 1-9, 2012, doi: 10.1371/journal.pone.0034610.

[4] Z. Xiong, "Cold Atmospheric Pressure Plasmas (CAPs) for Skin Wound Healing," Plasma Med.-Concepts Clin. Appl., 2018, doi: 10.5772/intechopen.76093.

[5] M. Bourdens et al., "Short exposure to cold atmospheric plasma induces senescence in human skin fibroblasts and adipose mesenchymal stromal cells," Sci. Rep., vol. 9, no. 1, pp. 1-15, December 2019, doi: 10.1038/s41598-019-45191-2.

[6] T. G. Klämpfl et al., "Cold atmospheric air plasma sterilization against spores and other microorganisms of clinical interest," Appl. Environ. Microbiol., vol. 78, no. 15, pp. 5077-582 August 2012, doi: 10.1128/AEM.00583-12.

The invention claimed is:

1. A plasma deposition system, comprising:
a microwave generator; and
a plurality of interchangeable waveguide conduit apparatuses, each configured to be separately coupled and used with the microwave generator, each waveguide conduit apparatus comprising:
a waveguide conduit that can be connected to and disconnected from the microwave generator, the waveguide conduit having a slot located at a first side thereof;
a primary plunger moveably positioned in the waveguide conduit for creating a primary standing microwave in the waveguide conduit;
an ejector apparatus disposed on a second side of the waveguide conduit opposite the slot on the first side thereof, the ejector apparatus including (1) an electrically conductive sleeve extending partially into the waveguide conduit, (2) a secondary plunger located concentrically around the electrically conductive sleeve for creating a secondary standing microwave in the ejector apparatus, and (3) an electrically insulating pipe connected to a gas supply source and positioned concentrically within the electrically conductive sleeve, the electrically insulating pipe having a tapered distal tip extending through the slot for discharging plasma to be deposited on a surface;
wherein the ejector apparatus is circular-shaped and is configured to discharge a narrow beam of plasma to be deposited on a spot of the surface;
wherein at least some of the plurality of waveguide conduit apparatuses further comprise one or more additional ejector apparatuses configured to discharge multiple beams of plasma to be deposited on an area of the surface.

2. The system of claim 1, further comprising a plasma diffuser chamber receiving the plasma from the electrically insulating pipe of a waveguide conduit apparatus connected to the microwave generator, the plasma diffuser chamber generating a shower of plasma beams to be applied on the surface.

3. The system of claim 2, further comprising a membrane plate stack configured to receive the plasma beams from the plasma diffuser chamber, the membrane plate stack comprising a plurality of membrane-covered structures facing each other in a generally parallel arrangement and being spaced apart to define a channel therebetween exposed to the plasma beams, each membrane-covered structure comprising a structure and a membrane covering outer surfaces of the structure with a gap therebetween through which a medium intended to be injected into a tissue is flowed.

4. The system of claim 2, wherein the plasma is directed towards a liquid bath containing a medium.

5. The system of claim 1, wherein the waveguide conduits of at least some of the plurality of waveguide conduit apparatuses are flexible.

6. The system of claim 1, wherein the waveguide conduits of at least some of the plurality of waveguide conduit apparatuses are bent to conform to a curved surface.

7. A plasma deposition system, comprising:
a microwave generator; and
a plurality of interchangeable waveguide conduit apparatuses, each configured to be separately coupled and used with the microwave generator, each waveguide conduit apparatus comprising:
a waveguide conduit that can be connected to and disconnected from the microwave generator, the waveguide conduit having a slot located at a first side thereof;
a primary plunger moveably positioned in the waveguide conduit for creating a primary standing microwave in the waveguide conduit;
an ejector apparatus disposed on a second side of the waveguide conduit opposite the slot on the first side thereof, the ejector apparatus including (1) an electrically conductive sleeve extending partially into the waveguide conduit, (2) a secondary plunger located concentrically around the electrically conductive sleeve for creating a secondary standing microwave in the ejector apparatus, and (3) an electrically insulating pipe connected to a gas supply source and positioned concentrically within the electrically conductive sleeve, the electrically insulating pipe having a tapered distal tip extending through the slot for discharging plasma to be deposited on a surface;
wherein the ejector apparatus is oblong-shaped and is configured to discharge a flat beam of plasma to be deposited on an area of the surface;
wherein at least some of the plurality of waveguide conduit apparatuses further comprise one or more additional ejector apparatuses configured to discharge multiple beams of plasma to be deposited on an area of the surface.

8. The system of claim 7, further comprising a plasma diffuser chamber receiving the plasma from the electrically insulating pipe of a waveguide conduit apparatus connected to the microwave generator, the plasma diffuser chamber generating a shower of plasma beams to be applied on the surface.

9. The system of claim 8, further comprising a membrane plate stack configured to receive the plasma beams from the plasma diffuser chamber, the membrane plate stack comprising a plurality of membrane-covered structures facing each other in a generally parallel arrangement and being spaced apart to define a channel therebetween exposed to the plasma beams, each membrane-covered structure comprising a structure and a membrane covering outer surfaces of the structure with a gap therebetween through which a medium intended to be injected into a tissue is flowed.

10. The system of claim 8, wherein the plasma is directed towards a liquid bath containing a medium.

11. The system of claim 7, wherein the waveguide conduits of at least some of the plurality of waveguide conduit apparatuses are flexible.

12. The system of claim 7, wherein the waveguide conduits of at least some of the plurality of waveguide conduit apparatuses are bent to conform to a curved surface.

* * * * *